(12) United States Patent
Shanafelter

(10) Patent No.: US 8,137,621 B2
(45) Date of Patent: Mar. 20, 2012

(54) SAMPLE CARRIER FOR AUTOMATIC LOADING OF SAMPLE TUBES FOR CLINICAL ANALYZER

(75) Inventor: Ronald J. Shanafelter, Fremont, CA (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 12/694,558

(22) Filed: Jan. 27, 2010

(65) Prior Publication Data

US 2010/0129262 A1 May 27, 2010

Related U.S. Application Data

(62) Division of application No. 11/961,343, filed on Dec. 20, 2007, now Pat. No. 7,678,331.

(51) Int. Cl.
*G01N 21/00* (2006.01)

(52) U.S. Cl. ........................................... 422/63

(58) Field of Classification Search .................... 422/65, 422/63, 102, 104, 105; 73/863.91, 863.92, 73/863.81, 863.82, 863.23; 366/220
See application file for complete search history.

(56) References Cited

U.S. PATENT DOCUMENTS

| | | |
|---|---|---|
| 3,747,900 A | 7/1973 | Dilts |
| 3,883,305 A | 5/1975 | Hoskins et al. |
| 4,146,364 A | 3/1979 | McCormick |
| 4,609,017 A | 9/1986 | Coulter et al. |
| 5,578,268 A | 11/1996 | Champseix et al. |
| 5,631,165 A | 5/1997 | Chupp et al. |
| 5,631,730 A | 5/1997 | Chupp et al. |
| 5,656,499 A | 8/1997 | Chupp et al. |

(Continued)

FOREIGN PATENT DOCUMENTS

EP 0549573 6/1993

(Continued)

OTHER PUBLICATIONS

Abbott Diagnostics. CELL-DYN® Sapphire™. Products [online], Abbott Laboratories, 2007 [retrieved on Nov. 25, 2007]. Retrieved from the Internet: <URL:http://www.abbottdiagnostics.com/Products/Instruments_by_Platform/default.cfm?system=CELLDYN&suffix=Sapphire>.

(Continued)

*Primary Examiner* — Hezron E Williams
*Assistant Examiner* — Nathaniel Kolb
(74) *Attorney, Agent, or Firm* — Hanley, Flight & Zimmerman, LLC

(57) ABSTRACT

A module for staging sample tubes and mixing the samples contained in the sample tubes for an automated clinical analyzer. In one embodiment, this module comprises a mixing drum, which is capable of mixing the contents of a sample tube in an end-over-end manner. The mixing drum is capable of mixing samples in the sample tubes without separating the solid components of the sample, e.g., red blood cells from the liquid components of the sample, e.g., plasma. A device for elevating the sample tube in the sample tube carrier can be used to enable the cap of the sample tube to be punctured by a piercing element in a piercing assembly. After the cap of the sample tube is punctured, a probe for aspirating the sample from said sample tube can obtain the sample in the receptacle of the sample tube through a bore in the piercing element. The piercing assembly can include a resiliently biased element for ejecting the sample tube from the piercing assembly.

20 Claims, 25 Drawing Sheets

U.S. PATENT DOCUMENTS

| | | | |
|---|---|---|---|
| 5,812,419 | A | 9/1998 | Chupp et al. |
| 5,891,734 | A | 4/1999 | Gill et al. |
| 5,939,326 | A | 8/1999 | Chupp et al. |
| 6,919,044 | B1 | 7/2005 | Shibata et al. |
| 7,858,032 | B2 | 12/2010 | Le Comte et al. |
| 2006/0093519 | A1 | 5/2006 | East |
| 2006/0286619 | A1 | 12/2006 | Ricci et al. |
| 2007/0110627 | A1 | 5/2007 | Nagai et al. |
| 2007/0134131 | A1* | 6/2007 | Watson et al. .................. 422/65 |
| 2007/0189926 | A1 | 8/2007 | Le Comte |
| 2008/0318306 | A1 | 12/2008 | Le Comte et al. |

FOREIGN PATENT DOCUMENTS

| | | |
|---|---|---|
| EP | 549573 A1 | 6/1993 |
| EP | 0688863 | 12/1995 |
| EP | 688863 A2 | 12/1995 |
| EP | 2232272 | 9/2010 |
| FR | 2867861 | 9/2005 |
| FR | 2867861 A1 | 9/2005 |
| WO | WO 2005/039767 A2 * | 5/2005 |

OTHER PUBLICATIONS

Abbott Diagnostics. CELL-DYN® 3200. Products [online]. Abbott Laboratories, 2007 [retrieved on Nov. 25, 2007] Retrieved from the Internet: <URL: http://www.abbottdiagnostics.com/Products/instruments%5Fby%5Fplatform/defaultcfm?sys_id=17>.

Abbott Diagnostics. CELL-DYN® 3700. Products [online]. Abbott Laboratories, 2007 [retrieved on Nov. 25, 2007] Retrieved from the Internet: <URL: http://www.abbottdiagnostics.com/Products/Instruments_by_Platform/default.cfm?system=CELL-DYN&suffix=3700>.

Fisher Scientific. Product Description [online]. Blood Tube Rotator [retrieved on Nov. 21, 2007] Retrieved from the Internet: <URL: http://design.hileytech.com/fisher/Stuartblood.html>.

Gecko Drive., Inc. Product Manual [online]. Stepper Motor Basics [retrieved on Apr. 9, 2008] Retrieved from the Internet:<URL:http://www.geckodrive.com/photos/Step_motor_basics.pdf>.

Invitation to Pay Additional Fees and, Where Applicable, Protest Fee, May 29, 2009.

ManSci Inc., Products [online]. Mini LabRoller™ Rotator [retrieved on Nov. 21, 2007] Retrieved from the Internet: <URL:http://www.mansci.com/products/mini%5Flabroller/>.

Nook Industries., Inc. Products [online]. Acme & Lead Screw Assembly Glossary and Technical Data [retrieved on Nov. 25, 2007] Retrieved from the Internet: <URL: http://www.nookindustries.com/Acme/AcmeGlossary.cfm>.

Select BioProducts. Catalog [online]. Tube Tumbler Rotator [retrieved on Nov. 21, 2007] Retrieved from the Internet:<URL: http://www.selectbioproducts.com/product-mix-tube.html>.

Wikipedia. Encyclopedia [online]. Stepper Motor [retrieved on Nov. 28, 2007] Retrieved from the Internet:<URL: http://en.wikipedia.org/wiki/Stepper_motor>.

European Office Action, issued by the European Patent Office in connection with European Application No. 08867839.6-1234, on Feb. 17, 2011, 7 pages.

Notice of Allowance, issued by the United States Patent and Trademark Office in connection with U.S. Appl. No. 11/961,343, filed Nov. 19, 2009, 12 pages.

* cited by examiner

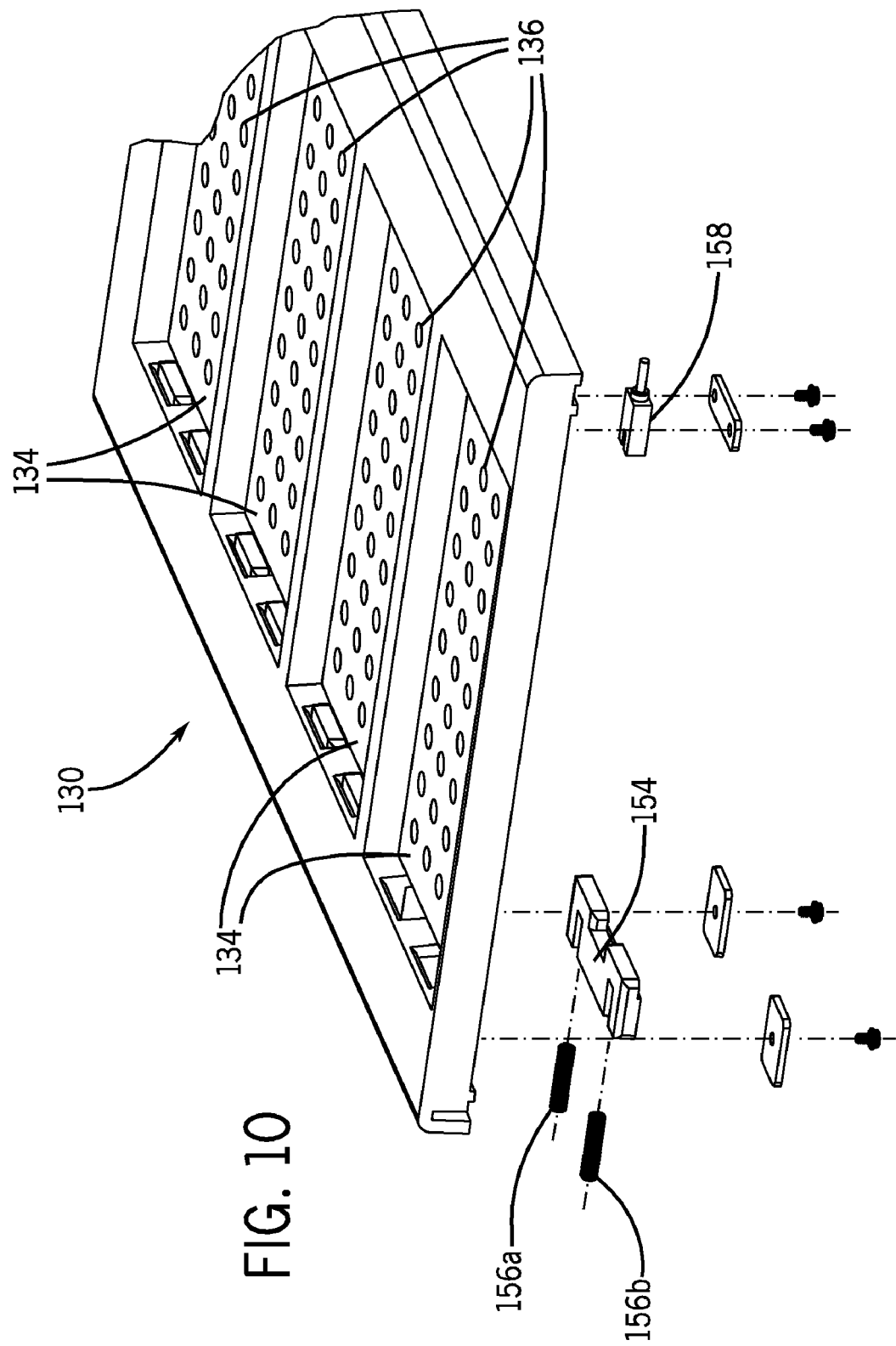

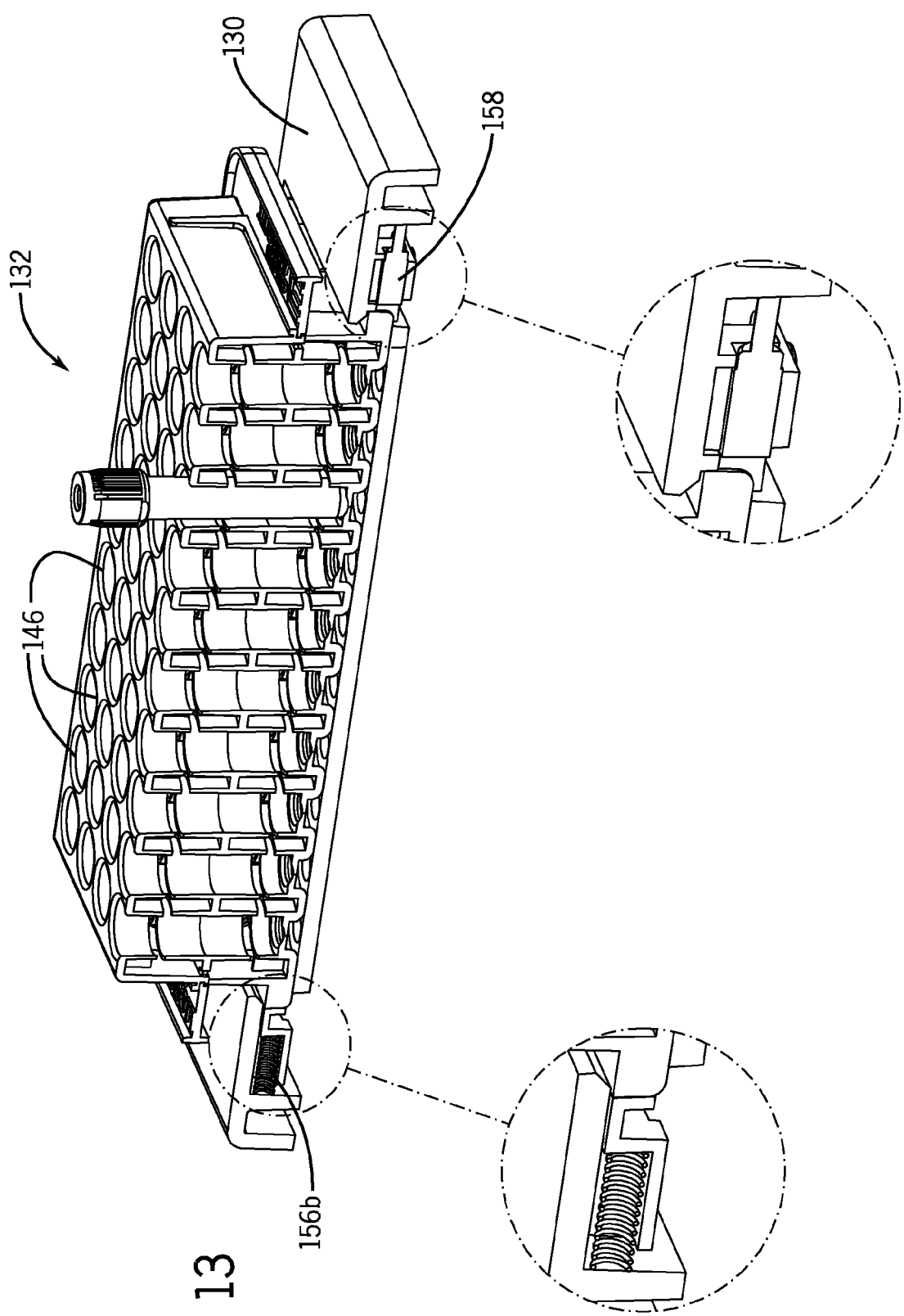

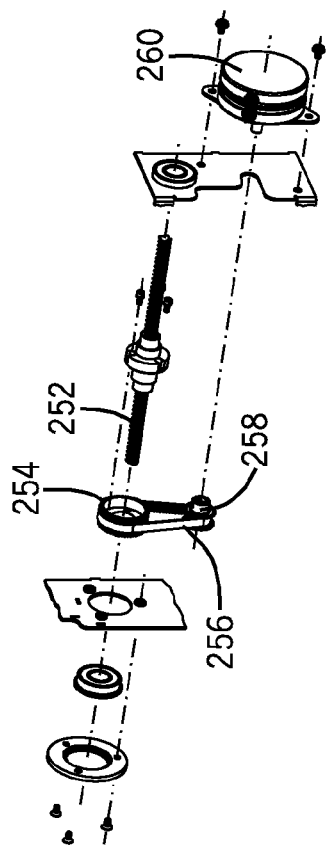
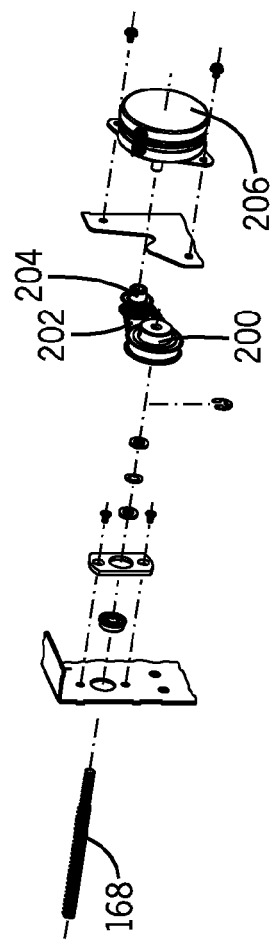
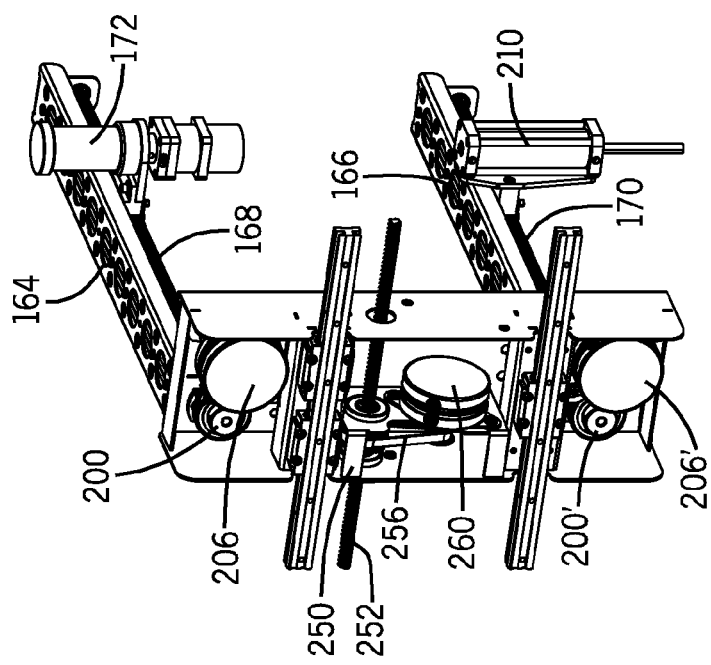
FIG. 17
FIG. 18
FIG. 16

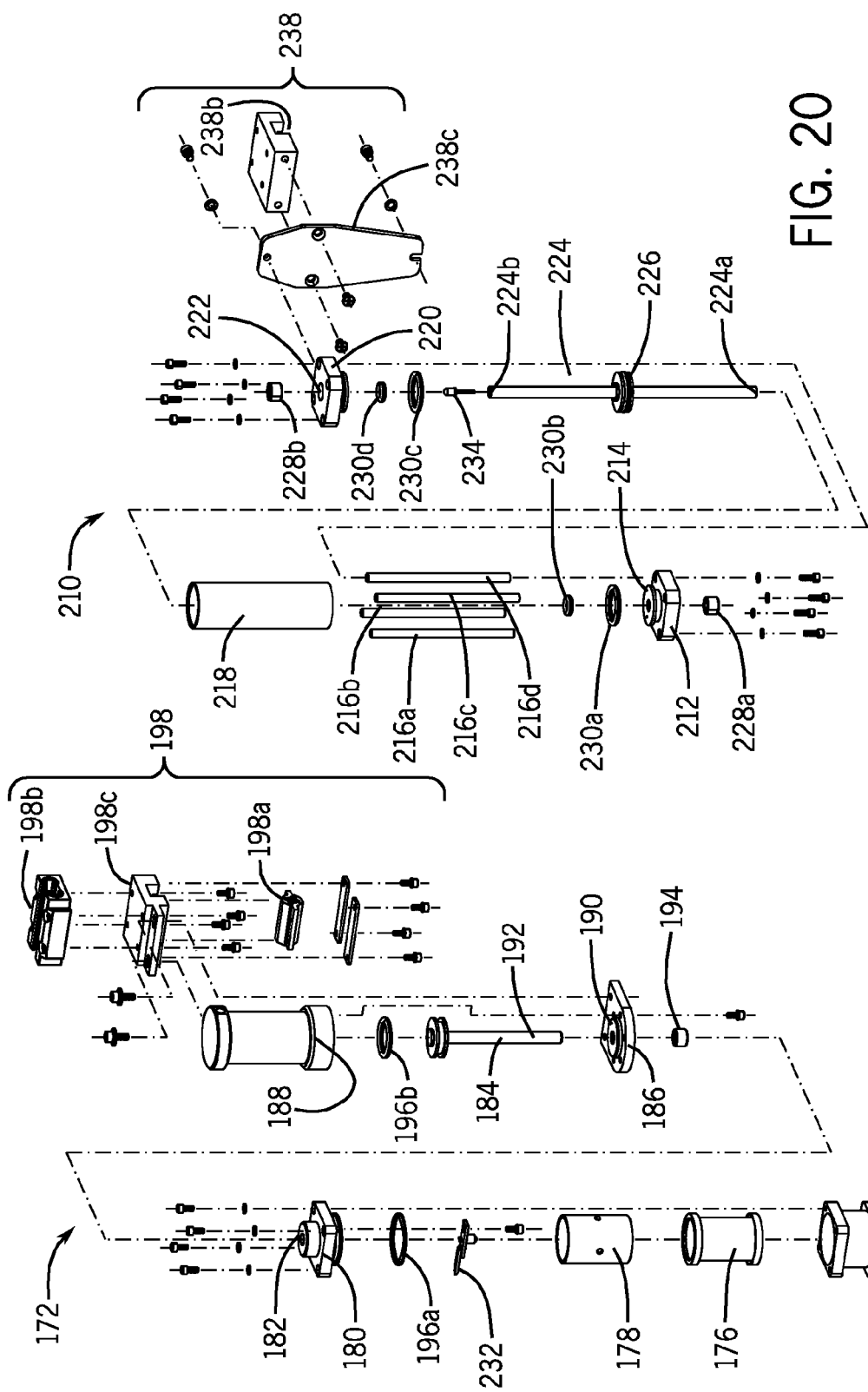

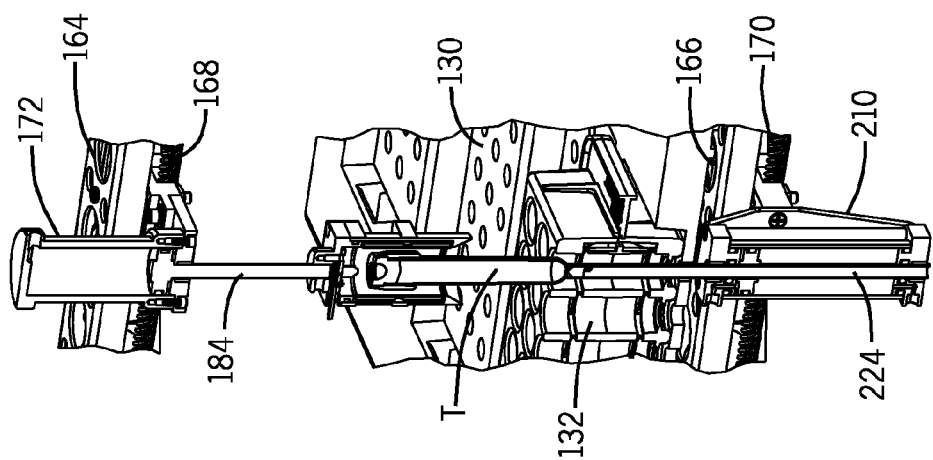
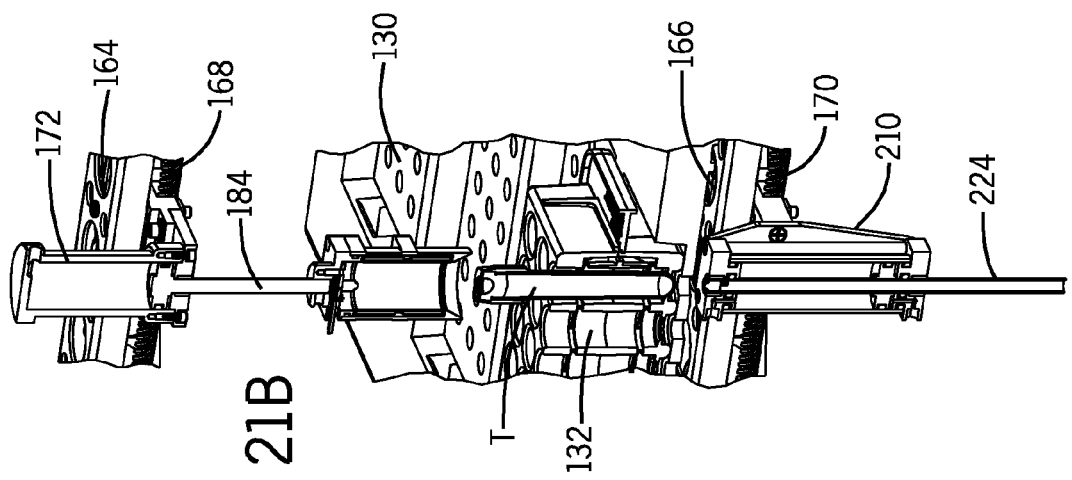
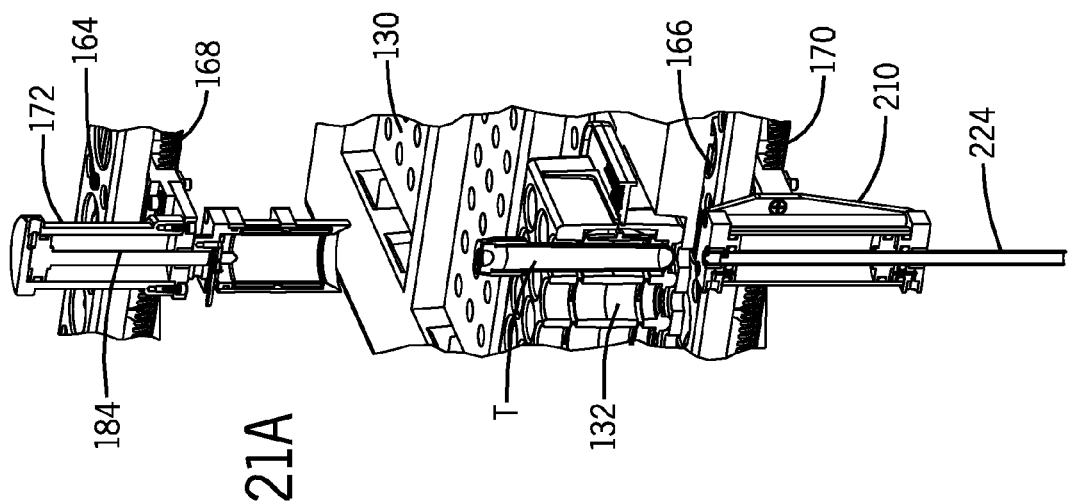

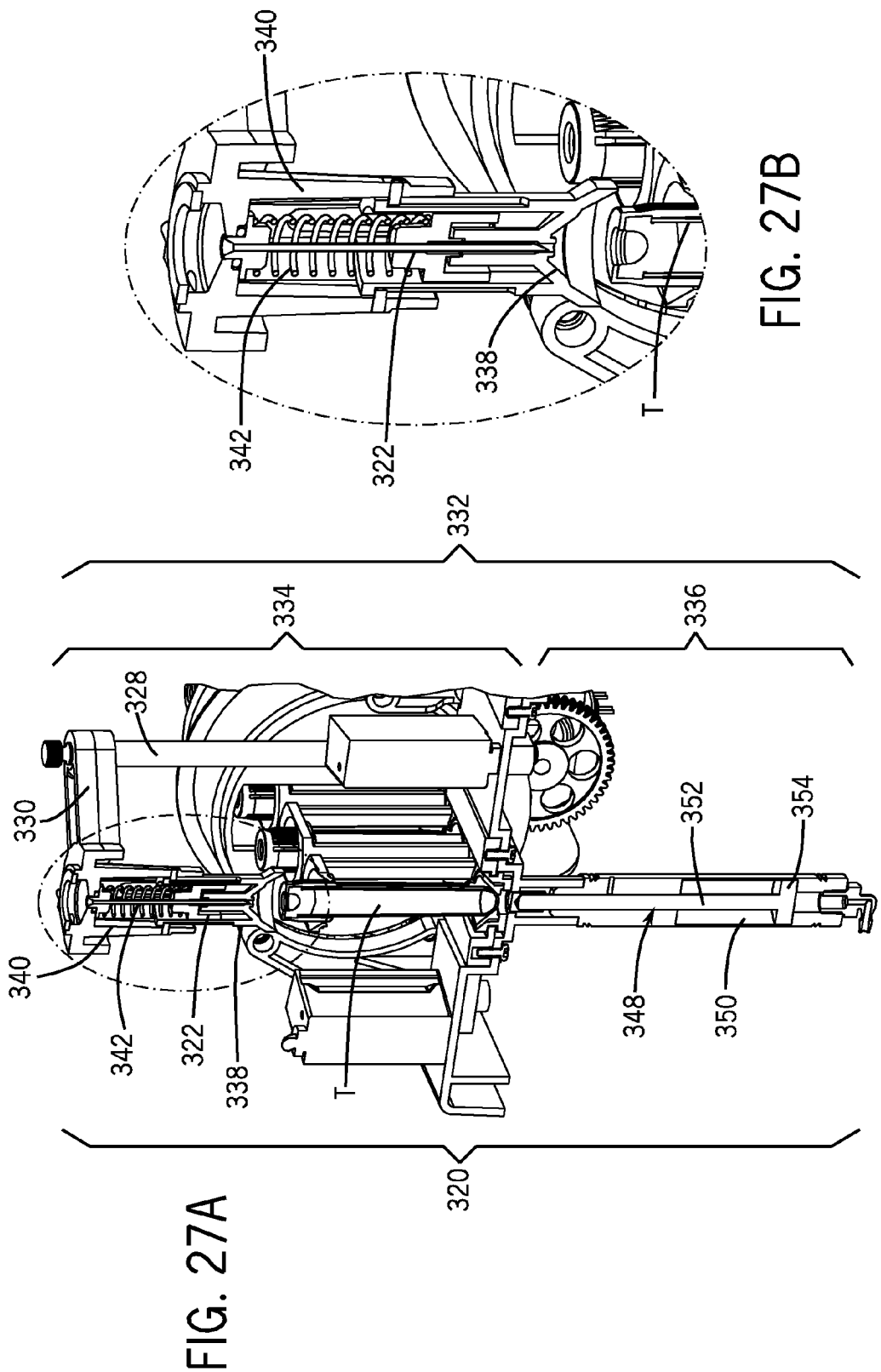

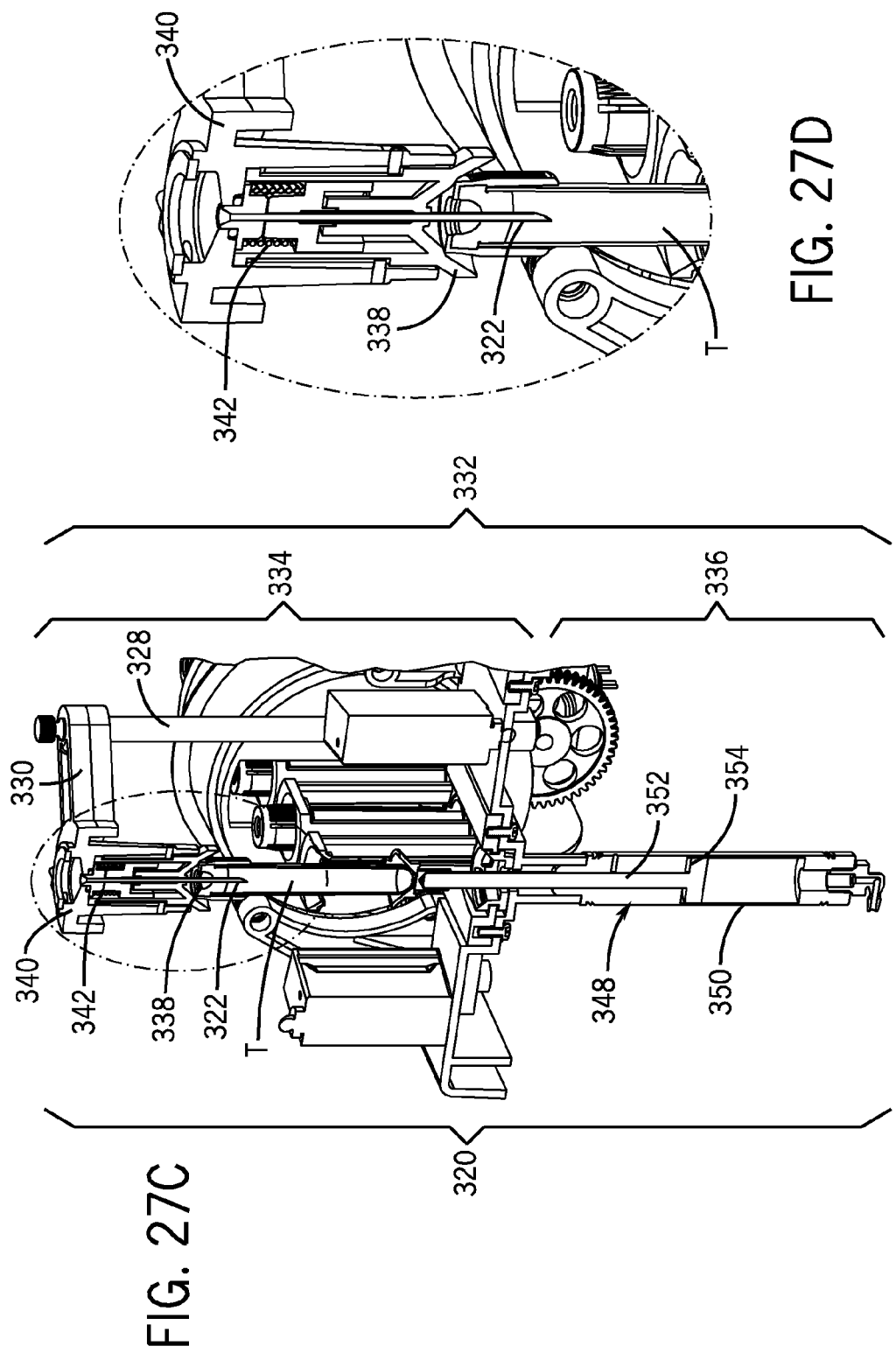

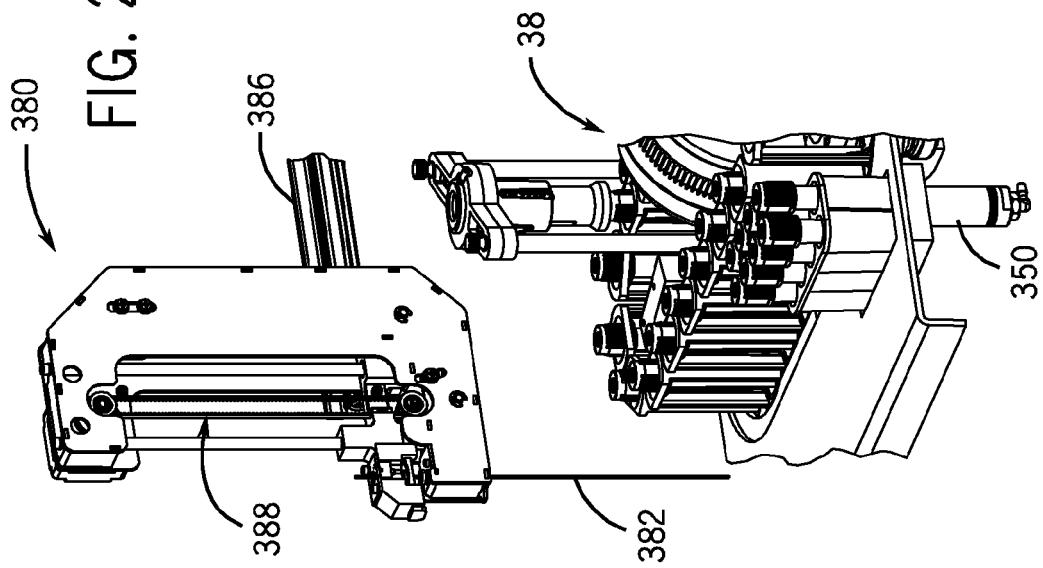
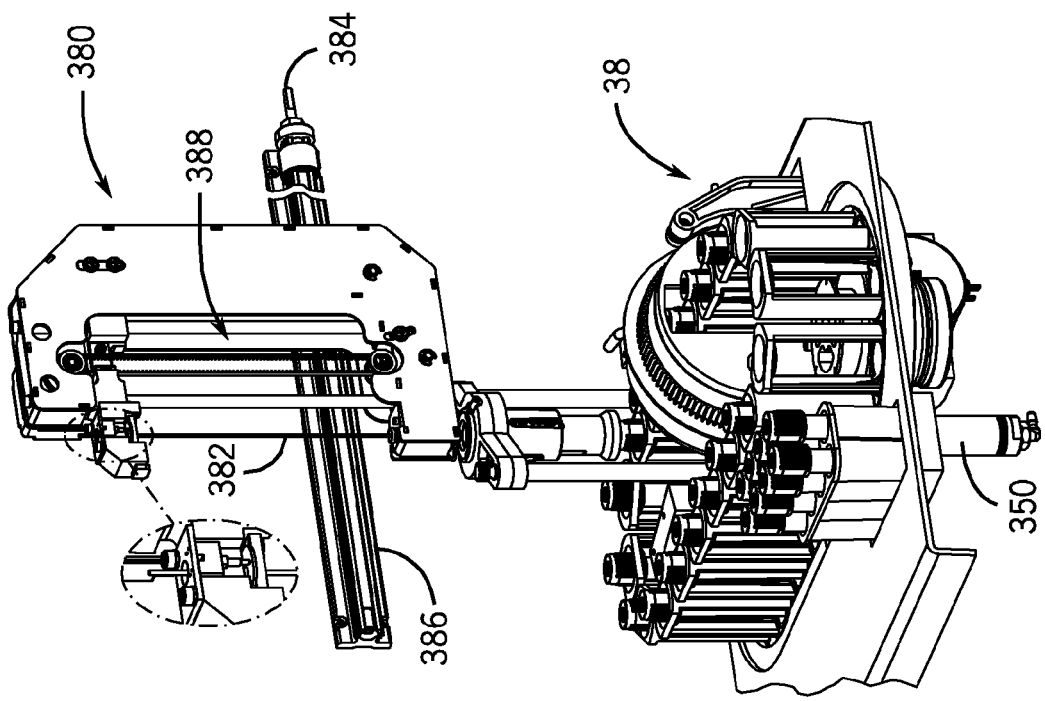

SAMPLE CARRIER FOR AUTOMATIC LOADING OF SAMPLE TUBES FOR CLINICAL ANALYZER

RELATED APPLICATIONS

This application is a divisional application of U.S. patent application Ser. No. 11/961,343, filed Dec. 20, 2007.

BACKGROUND OF THE INVENTION

1. Field of the Invention

This invention relates to automated clinical analyzers, more particularly, automatic loading of sample tubes into an automated clinical analyzer.

2. Discussion of the Art

It is common for automated clinical analyzers for in vitro diagnostic testing to employ automated processes for handling biological samples. It is common for sample containers to be held in a sample tube rack that holds a plurality of sample containers. Sample containers are typically loaded into positions in a sample tube rack prior to the sample tube rack being introduced to an automated clinical analyzer. The sample containers remain in the sample tube rack until the automated clinical analyzer has completed processing, whereupon the sample containers, still in their original positions in the sample tube rack, are removed from the automated clinical analyzer for subsequent storage or further processing, also known as reprocessing.

Currently, a well-known sample loading system for loading sample tubes into an automated clinical analyzer comprises a sample tube rack that contains ten (10) sample tubes. At various times, the sample tubes arrive at the incorrect position in the automated clinical analyzer. Because of this problem, manual handling of sample tubes is required more often than is preferred. In the current sample loading system, the sample tubes in the sample tube racks are positioned very close together. Because the sample tube stands at a slight incline from a vertical orientation, it is difficult for a robot that travels in only horizontal planes and a vertical plane (i.e., X-direction, Y-direction, Z-direction) to obtain access to a sample tube in the sample tube rack. It is also difficult to mix samples while the sample tubes are in the sample tube racks in the staging area.

U.S. Pat. No. 3,747,900 discloses means for controllably oscillating blood specimen containers comprising support means, motor means mounted on the support means, a plate drivingly connected to the motor means and mounted for rotation relative to the support means, and means for removably fastening such containers to the plate for movement therewith. U.S. Pat. No. 4,146,364 discloses a mixing apparatus particularly adapted for mixing blood cell suspensions and which includes a support platform having discrete troughs adapted to receive a plurality of specimen container tubes and effect rocking of the tubes to uniformly mix blood cell suspensions without distorting, breaking or foaming the suspensions. The platform may be randomly loaded with specimen tubes and is adapted to effect rocking of the platform in response to the presence of a tube within a trough, and provides first signals indicating the presence of tubes within the individual troughs and second signals indicating lapse of a predetermined mixing time for each specimen tube. U.S. Pat. No. 6,919,044 discloses a front-end system that accepts samples and selectively provides aliquots of those samples to selected clinical chemistry analyzers coupled to the front-end system. The front-end system is coupled to an assembly of one or more clinical chemistry analyzers that might provide complementary analytical tools so that the overall system of front-end system and clinical chemistry analyzers provides a pre-determined broad range of clinical analytical testing. The testing protocols for samples input to the overall system can be independently determined. Any sample may undergo a test within one or more of the clinical chemistry analyzers or a series of tests within a single or more typically within plural ones of the analyzers, depending upon the testing sequence defined for that sample. None of the foregoing patents addresses the problems previously identified.

In view of the foregoing difficulties, it would be desirable to develop a system for loading samples into an automated clinical analyzer that reduces the incidences of incorrect positioning of the sample tubes, reduces the difficulty of access of a robotic mechanism to the sample tubes, and simplifies the mixing of samples in the sample tubes in the staging area.

SUMMARY OF THE INVENTION

In one aspect, this invention provides a module for staging sample tubes and mixing the samples contained in the sample tubes for an automated clinical analyzer. The sample tubes have a receptacle and a cap. In one embodiment, this module comprises a mixing drum, which is capable of mixing the contents of a sample tube in an end-over-end manner. The mixing drum is capable of mixing samples in the sample tubes without separating the solid components of the sample, e.g., red blood cells from the liquid components of the sample, e.g., plasma. In this embodiment, the module comprises a track associated with a mixing drum along which track sample tubes are carried in sample tube carriers. Sample tubes in sample tube carriers are transported along the track associated with the mixing drum into the mixing drum, where the sample in the sample tube is mixed. The mixing drum is positioned on the track. The mixing drum has a central axis, a first opening perpendicular to the central axis and a second opening perpendicular to the central axis. A sample tube carrier containing a sample tube can enter said first opening and emerge from said second opening. The mixing drum can rotate about is central axis to rotate the sample tubes end-over-end to mix the samples. After the sample is mixed, the sample tube carrier is transported out of the mixing drum to a venting assembly. At this venting assembly, the cap of the sample tube is punctured.

A device for elevating the sample tube in the sample tube carrier can be used to enable the cap of the sample tube to be punctured by a piercing element in a piercing assembly. After the cap of the sample tube is punctured, a probe for aspirating the sample from said sample tube can obtain the sample in the receptacle of the sample tube through a bore in the piercing element. The piercing assembly can include a resiliently biased element for ejecting the sample tube from the piercing assembly.

The mixing drum is capable of holding a plurality of sample tube carriers holding sample tubes. The module for staging sample tubes and mixing samples in the sample tubes can further include at least one device, e.g., a barcode reader, for reading information from the sample tubes.

In another embodiment, the system further comprises a module for selecting sample tubes from sample tube racks for holding the sample tubes and placing the sample tubes onto the module for staging sample tubes and mixing the samples in the sample tubes. The module for selecting sample tubes from the sample tube racks and placing the sample tubes onto the module for staging sample tubes and mixing the samples comprises at least one tray for holding at least one rack for holding sample tubes. The module for selecting sample tubes from the sample tube racks and placing the sample tubes onto the module for staging sample tubes and mixing the samples comprises a device for elevating a sample tube and transferring the elevated sample tube to the module for staging sample tubes and mixing the samples. The elevating device comprises a sample tube receiver and a sample tube lifter. The sample tube receiver and the sample tube lifter can be moved in the X-direction and the Y-direction by means of lead screws.

In still another aspect, this invention provides a carrier for a sample tube that can hold a sample tube as it is being transported into the mixing drum. The sample in the sample tube can be mixed by rotating the sample tube carrier and the sample tube held therein in an end-over-end manner. The carrier for the sample tube is designed in such a manner that the sample tube can be elevated from and lowered into the sample tube carrier by means of a piston positioned externally of the sample tube carrier.

In still another aspect, this invention provides a track system that can be used for transporting sample tubes to the module for staging sample tubes and mixing the contents of the sample tubes.

Other aspects of the invention described herein include method for using the aforementioned module for staging sample tubes and mixing the samples in the sample tubes and the aforementioned module for selecting sample tubes from the racks for holding the sample tubes and placing the sample tubes onto the module for staging sample tubes and mixing the samples in the sample tubes.

The system described herein is compact; only a small area is required to position (a) a module for staging sample tubes and mixing the samples in the sample tubes and (b) a module for selecting sample tubes from the racks for holding the sample tubes and placing the sample tubes onto the module for staging sample tubes and mixing the samples in the sample tubes. The system described herein enables the lifting of sample tubes from sample tube racks with little difficulty. Furthermore, the mixing of the contents of sample tubes can be carried out in the staging area.

BRIEF DESCRIPTION OF THE DRAWINGS

FIG. 10 is an exploded perspective view of a tray for holding racks for holding sample tubes.

FIG. 13 is a cross-sectional view, in perspective, through an assembly comprising the tray for holding sample tube racks for holding sample tubes shown in FIG. 10 and the sample tube rack for holding sample tubes shown in FIGS. 11 and 12.

FIG. 16 is a perspective view of a transmission system comprising a plurality of lead screw assemblies for moving certain components of a robotic mechanism that can be used for selecting sample tubes from the racks for holding the sample tubes and placing the sample tubes onto the module for staging sample tubes and mixing the samples in the sample tubes.

FIG. 17 is an exploded perspective view of a lead screw assembly for moving the upright element of a robotic mechanism along the longitudinal axis of the lead screw.

FIG. 18 is an exploded perspective view of a lead screw assembly for moving a sample tube receiver or a sample tube lifter along the longitudinal axis of the lead screw.

FIG. 19 is an exploded perspective view of a sample tube receiver.

FIG. 20 is an exploded perspective view of a sample tube lifter.

FIGS. 21A, 21B, 21C, 21D, 21E, 21F, 21G, 21H, and 21I are perspective views illustrating the components for selecting sample tubes from the module for selecting sample tubes from the racks for holding the sample tubes and placing the sample tubes onto the module for staging sample tubes and mixing the samples in the sample tubes. Each of FIGS. 21A, 21B, 21C, 21D, 21E, 21F, 21G, 21H, and 21I shows a portion of the sequence for selecting sample tubes from the module for selecting sample tubes from the racks for holding the sample tubes and placing the sample tubes onto the module for staging sample tubes and mixing the samples in the sample tubes.

FIG. 27A is a cross-sectional view, in perspective, illustrating the components for piercing the caps of sample tubes and venting the sample tubes, prior to the piercing step. FIG. 27B is a cross-sectional view, in perspective and greatly enlarged, illustrating the components for piercing the caps of sample tubes and venting the sample tubes, prior to the piercing step. FIG. 27C is a cross-sectional view, in perspective, illustrating the components for piercing the caps of sample tubes and venting the sample tubes, during the piercing step. FIG. 27D is a cross-sectional view, in perspective and greatly enlarged, illustrating the components for piercing the caps of sample tubes and venting the sample tubes, during the piercing step.

FIG. 28 is a perspective view illustrating an aspiration head in the closed mode position. The sample cannot be obtained from the sample tube when the aspiration head is in this position.

FIG. 29 is a perspective view illustrating the aspiration head shown in FIG. 28 in the open mode position. The sample can be obtained from the sample tube when the aspiration head is in this position.

DETAILED DESCRIPTION

Figure 1:
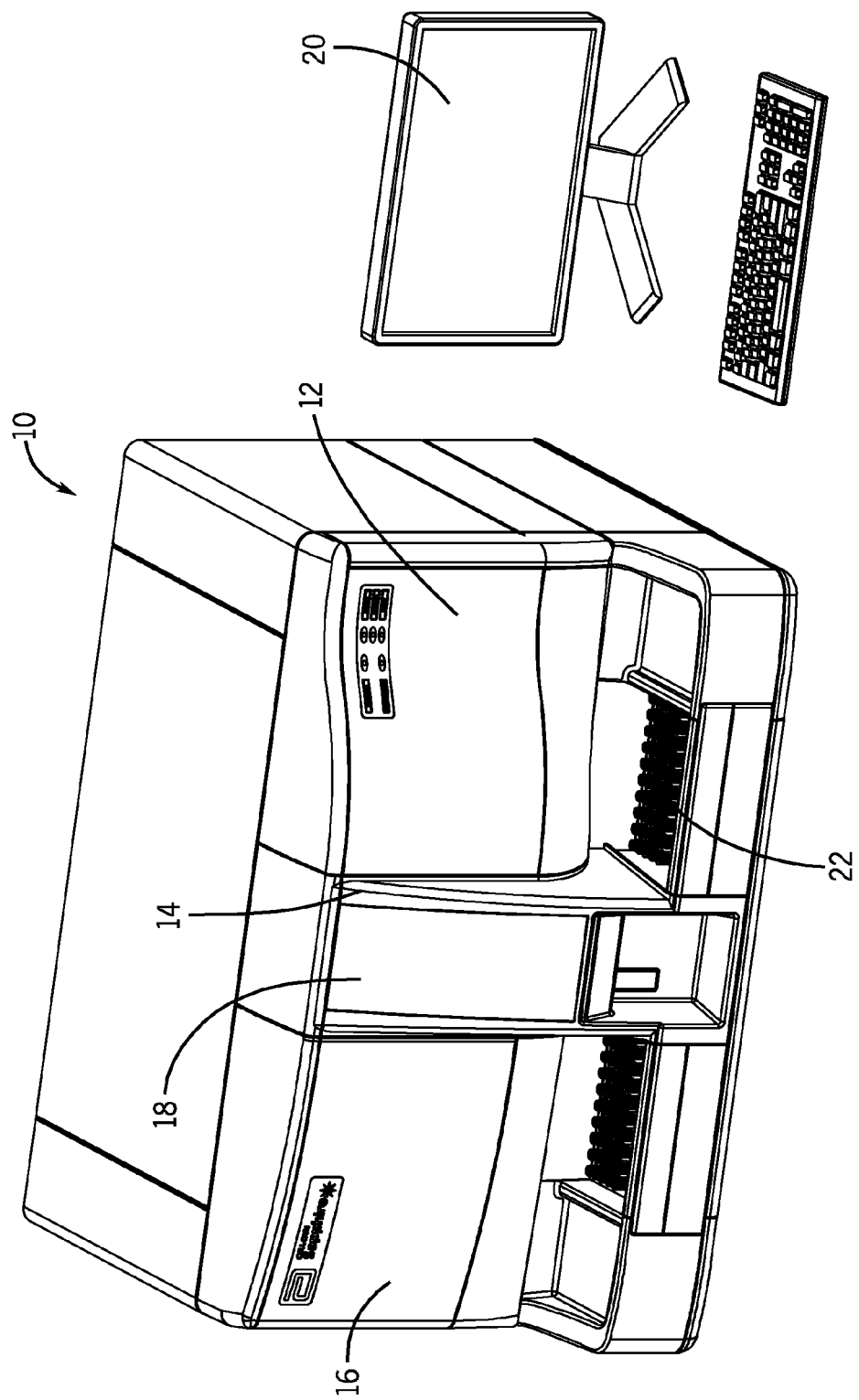
FIG. 1 is a front view in elevation illustrating an automated clinical analyzer, i.e., a hematology analyzer, which can be modified to employ the system for loading the sample tubes described herein.

As used herein, the expression "automated clinical analyzer" means a medical laboratory instrument designed to measure different analytes and other characteristics in a number of biological samples quickly, with minimal human assistance. As used herein, the expression "X-direction, Y-direction, Z-direction" refers to a device that can move in three directions, a first horizontal direction, a second horizontal direction that is perpendicular to the first horizontal direction, and a third direction that is perpendicular to both the first horizontal direction and the second horizontal direction. As used herein, the expression "staging area" means that portion of an analytical system where pre-analytical preparation of biological samples is carried out. As used herein, the expression "mixing drum" means a hollow, cylindrical article is which samples are combined or blended into one mass or mixture, rendering the constituent parts indistinguishable. As used herein, the expression "end-over-end" refers to rotating a container having a first end, a second end, at least one major surface between the first end and the second end, and an axis A-A that is parallel to both the first end and the second end and is equidistant from both the first end and the second end about that axis A-A. As used herein, the expression "aspiration head" means the assembly that supports an aspiration probe and controls the movement thereof. As used herein, the expression "aspiration probe" means a device that has the dual functions of removing liquids from sample tubes by suction and distributing portions of the liquids aspirated into reaction vessels. As used herein, the expression "sample tube receiver" means a device for holding the upper about 25% to about 50% of a sample tube when the sample tube is being transferred from a sample tube rack to a sample tube carrier, from a sample tube carrier to a sample tube rack, or from a sample tube carrier to another sample tube carrier. As used herein, the expression "sample tube lifter" means a device that lifts a sample tube from a sample tube carrier or from a sample tube rack so that the sample tube can be gripped by the sample tube receiver. As used herein, the expression "track system" refers to a track the extent of which is not limited to a single module, but extends across a plurality of modules. As used herein, the term "track" refers to a track the extent of which is limited to a single module. As used herein, the "carrier for a sample tube" is alternately referred to herein as "sample tube carrier." As used herein, the "rack for holding sample tubes", "sample tube rack for holding sample tubes", and the like, are alternately referred to herein as "sample tube rack."

So far as is possible, in the drawings, like parts have like reference numerals. In some cases, parts that are identical or are substantially similar, but which are utilized in different assemblies, have reference numerals that are distinguished by a prime mark, e.g., ('), ("), ("'). In those cases, the base reference numeral for subsequent mention(s) of an identical part or a substantially similar part remains the same, but the subsequent mention(s) of an identical part or a substantially similar part is designated by an appropriate prime mark.

For the sake of simplicity, when a plurality of identical or substantially similar items are depicted in a drawing, no more than four (4) of the identical or substantially similar items will be designated with the selected reference numeral. For example, it five (5) or more items of the same type are shown in a given drawing, no more than four (4) of the items will be designated with the reference numeral allocated to the item.

FIG. 1 shows an automated clinical analyzer 10 that can be modified for use with the loading system described herein. Although this automated clinical analyzer is a hematology analyzer, it should be noted that use of the sample tube rack described herein is not limited to hematology analyzers. Automated clinical analyzers contemplated for use with this invention include, but are not limited to, CELL-DYN® Sapphire, CELL-DYN® 3700, and CELL-DYN® 3200. These automated clinical analyzers are commercially available from Abbott Laboratories, Abbott Park, Ill. Descriptions of these analyzers can be found in U.S. Pat. Nos. 5,939,326; 5,891,734; 5,812,419; 5,656,499; 5,631,165; 5,631,730, all of which are incorporated herein by reference. The automated clinical analyzer 10 comprises an input section 12, an analysis section 14, and an output section 16. The analysis section 14 comprises one or more devices for aspirating at least a portion of a sample of blood, diluting the portion of the sample aspirated to the required concentration, and examining the characteristics of the diluted sample by means of optical or electrical measurements or both optical and electrical measurements. The location where samples are aspirated is indicated by the reference numeral 18. The analysis section 14 is electrically connected to a controller/data processing module 20 for controlling the processes of the automated clinical analyzer 10 and processing data obtained from the analysis section 14. The controller/data processing module 20 contains software for controlling the instrument processes and generating a report of the results of the analysis section 14. A sample tube rack 22 from a plurality of sample tube racks is introduced to the automated clinical analyzer 10 by way of the input section 12. After the samples in the sample tube rack 22 are analyzed in the analysis section 14, the sample tube rack 22 is transferred to the output section 16. The invention described herein eliminates the use of the sample tube rack 22.

Figure 2:
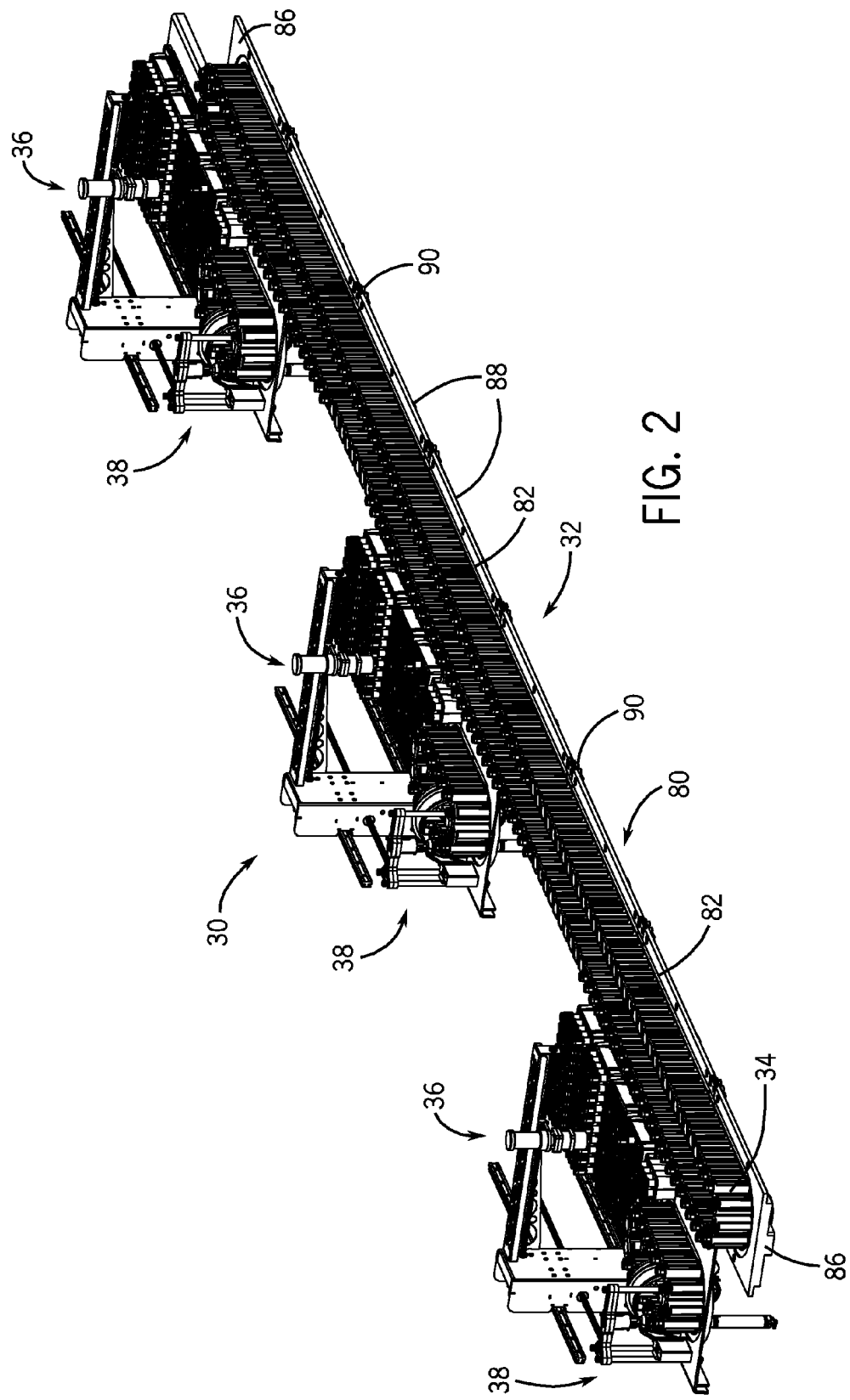
FIG. 2 is a perspective view of a modular track system, a module for staging sample tubes and mixing the samples in the sample tubes, and a module for selecting sample tubes from the racks for holding the sample tubes and placing the sample tubes onto the module for staging sample tubes and mixing the samples in the sample tubes.

FIG. 2 shows a system 30 for transferring sample tubes "T" to or from, or both to and from, an automated clinical analyzer. The system 30 comprises a track system 32, which conveys sample tube carriers 34 that hold sample tubes "T", a module 36 for selecting sample tubes from the racks for holding the sample tubes and placing the sample tubes onto a module 38 for staging sample tubes and mixing the samples in the sample tubes. For the sake of ease of reading the detailed description of this specification, the module 36 for selecting sample tubes from the racks for holding the sample tubes and placing the sample tubes onto a module 38 for staging sample tubes and mixing the samples in the sample tubes will alternately be referred to herein as "the module 36 for selecting sample tubes and placing sample tubes", and the module 38 for staging sample tubes and mixing the samples in the sample tubes will alternately be referred to herein as "the module for staging sample tubes and mixing samples." The module 36 for selecting sample tubes and placing sample tubes enables the sample tubes "T" to be temporarily stored in sample tube racks until the sample tubes "T" are transferred to the module 38 for staging sample tubes and mixing samples. The module 38 for staging sample tubes and mixing samples receives sample tubes "T" from the sample tube racks (or from sample tube carriers 34), mixes the samples in the sample tubes "T", and holds the sample tubes "T" containing the mixed samples until the mixed samples are transferred to an automated clinical analyzer, where the samples in the sample tubes "T" undergo diagnostic tests.

Figure 3:
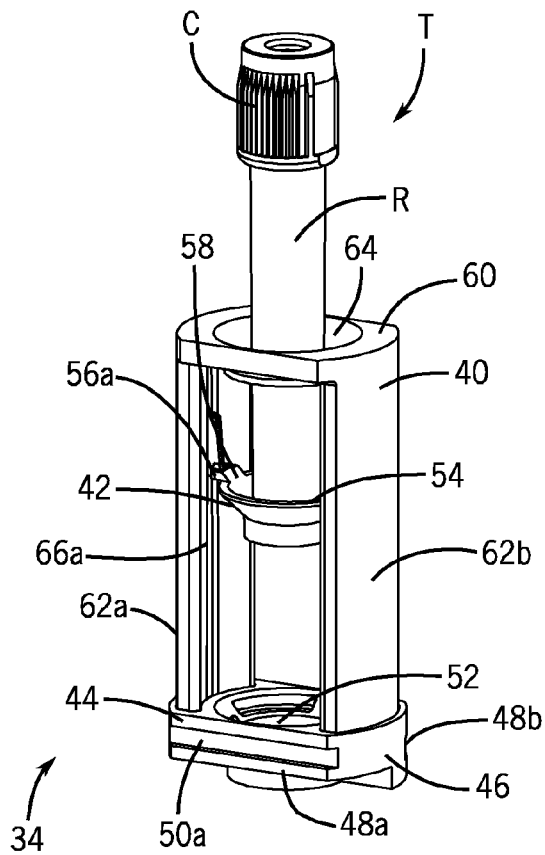
FIG. 3 is a perspective view of a carrier for sample tubes.
Figure 4:
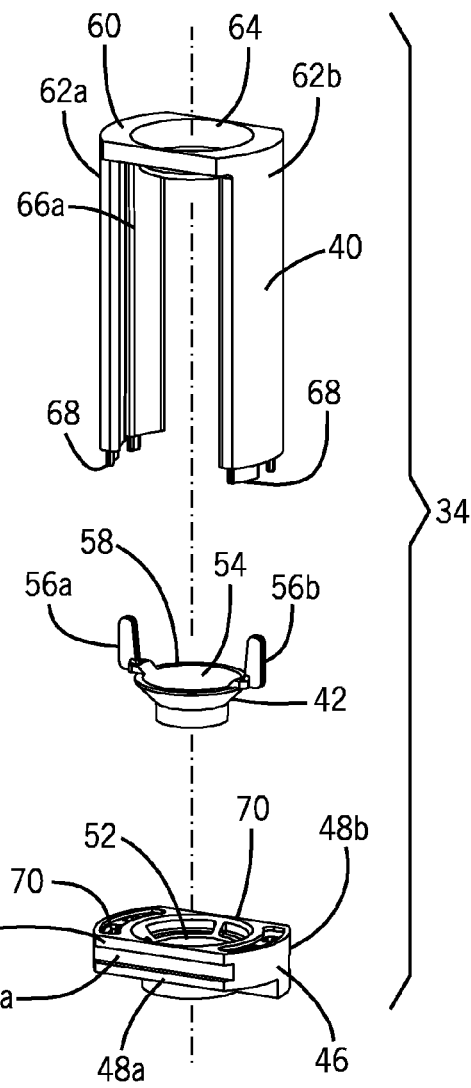
FIG. 4 is an exploded perspective view of the carrier shown in FIG. 3.

Referring now to FIGS. 3 and 4, the track system 32 is used for conveying a large number of sample tube carriers 34 that hold sample tubes "T". Each sample tube carrier 34 is designed in such a manner that it can support a sample tube "T" in a substantially vertical orientation. FIG. 3 shows a sample tube "T", which comprises a receptacle "R" for holding a liquid sample and a cap "C" for preventing the liquid sample from escaping the receptacle "R", either by spillage or by evaporation. The receptacle "R" is typically formed from a polymeric material. The cap "C" typically comprises polymeric material than can be pierced by a metallic needle.

As shown in FIGS. 3 and 4, a sample tube carrier 34 comprises a body 40, a sample tube bottom retainer 42, and a base 44. The purpose of the base 44 is to support the body 40. The purpose of the body 40 is to support the sample tube "T". The purpose of the sample tube bottom retainer 42 is to properly align the bottom of a sample tube "T". As shown in FIGS. 3 and 4, the base 44 has a substantially cylindrical body 46, with two segments 48a, 48b of the body 46 being truncated. The truncated segment 48a has a groove 50a formed therein. The truncated segment 48b has a groove 50b (see FIG. 15) formed therein. The substantially cylindrical body 46 has an opening 52 formed therethrough. The sample tube bottom retainer 42 has a body 54 having a pair of tabs 56a, 56b rising upwardly from the uppermost surface 58 of the sample tube bottom retainer 42. The uppermost surface 58 of the sample tube bottom retainer 42 is concave, to better retain the bottom of the sample tube "T". The body 40 of the sample tube carrier 34 comprises an upper substantially cylindrical portion 60 from which a pair of elongated upright portions 62a, 62b depend. The upper substantially cylindrical portion 60 has an opening 64 formed therethrough. It is preferred that the opening 64 have beveled edges. In the elongated upright portion 62a is a first elongated groove 66a, and in the elongated upright portion 62b is a second elongated groove (not shown) that is a mirror image of the first elongated groove 66a. The tab 56a fits into the groove 66a and the tab 56b fits into the groove 66b. The tabs 56a, 56b are capable of sliding in the grooves 66a, 66b, respectively. As can be seen in FIG. 4, projections 68 fit into slots 70 in the base 44.

The sample tube bottom retainer 42 is normally in contact with the base 44. However, for certain operations that must be carried out to utilize the various modules described herein, it is necessary for the sample tube bottom retainer 42 to be elevated so that the upper half of the sample tube "T" retained on the sample tube bottom retainer 42 projects above the uppermost portion of the body 40. Such operations, include, for example, removing the sample tube "T" from the sample tube carrier 34 by means of a sample tube receiver, which will be described later, inserting the sample tube "T" into the sample tube carrier 34, which will be described later. When the sample tube bottom retainer 42 is elevated, and subsequently, lowered, the tabs 56a, 56b move within the grooves 66a, 66b, respectively, so that the sample tube bottom retainer 42 maintains its initial orientation with respect to the vertical axis of the sample tube carrier 34, i.e., the orientation when the sample tube bottom retainer 42 rests on the base 44. The function of the opening 52 is to allow access of a piston, the function of which piston is to raise the sample tube bottom retainer 34 and to allow gentle lowering of the sample tube bottom retainer 42. The operation of the aforementioned piston will be described later. The function of the opening 64 is to allow the sample tube "T" to obtain access to the sample tube carrier 34. The edge of the opening 64 is preferably beveled so that the sample tube "T" can obtain access to the sample tube carrier 34 through the opening 64 even if the axis of the sample tube "T" is not in perfect alignment with the axis of the sample tube carrier 34. The groove 50a and the groove 50b in the base 44 engage ridges in the guide rails of the various sections of the track where sample tube carriers are used. These ridges and guide rails will be described later.

Referring now to FIGS. 2, 5, 6, 7, 8, 9, and 15, the track system 32 includes a track 80 that is bounded by an outer guide rail 82 and an inner guide rail 84. See FIG. 15. The track 80 can be a conventional track having a first end section 86 and a second end section 86, which is substantially identical to the first end section 86. Between the first end section 86 and the second end section 86 is at least one straight section 88. The track 80 can further include other sections, such as for example, one or more joining sections 90, and one or more corner sections 92.

Figure 5:
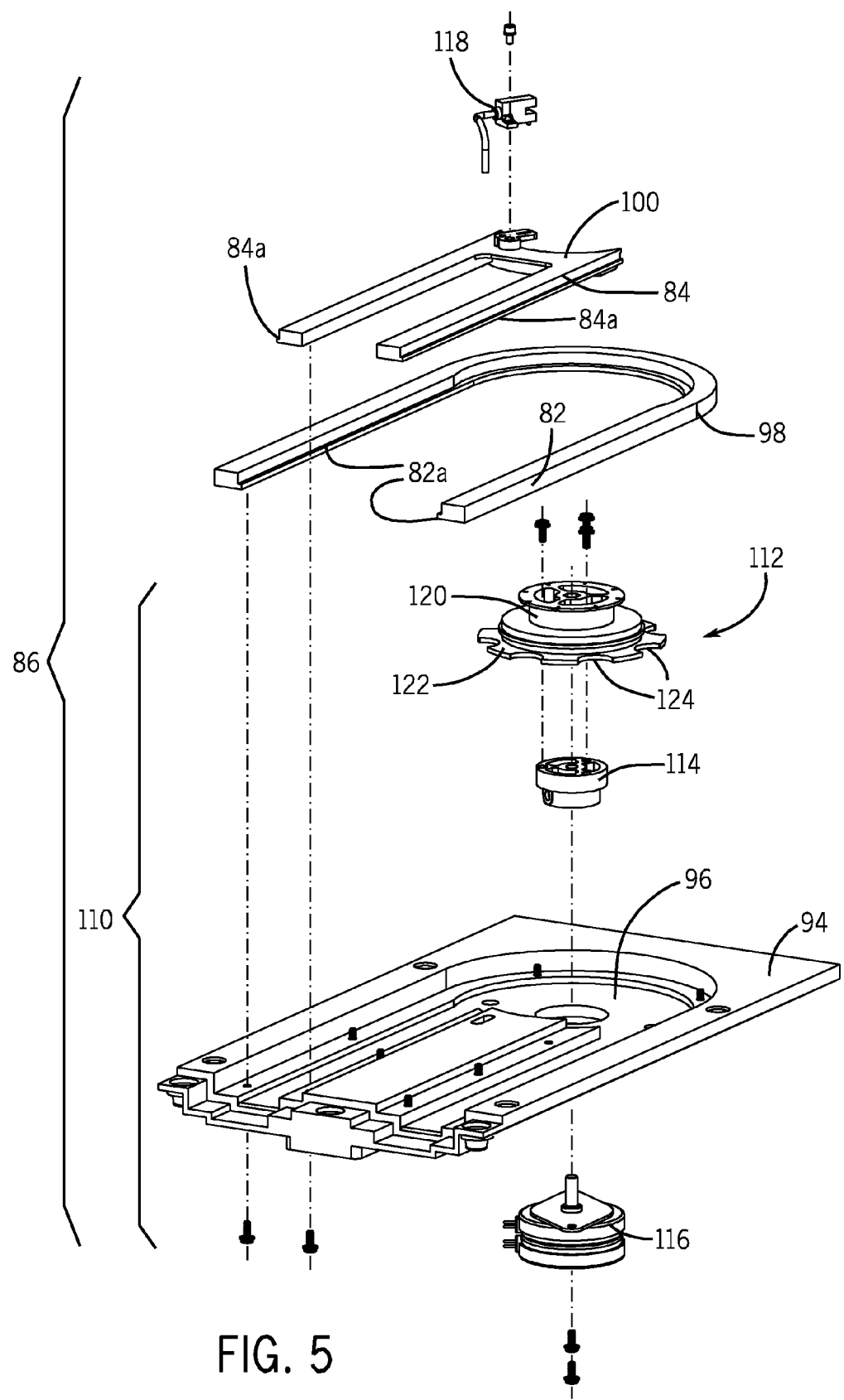
FIG. 5 is an exploded perspective view of an end section of a drive system for moving carriers for sample tubes.

Referring now to FIG. 5, an end section 86 comprises a base 94, which contains a recessed area 96 for defining the path upon which sample tube carriers 34 travel. The outer guide rail 82 is formed by a first U-shaped element 98, which is mounted onto the base 94 and fastened to the base 94, typically by means of bolts. The inner guide rail 84 is formed by a second U-shaped element 100, which is mounted onto the base 94 and fastened to the base 94, typically by means of bolts. The outer guide rail 82 has a ridge 82a formed on the surface thereof facing the inner guide rail 84, and the inner guide rail 84 has a ridge 84a formed on the surface thereof facing the outer guide rail 82. The portion of the first U-shaped element 98 between the parallel arms of the U-shape is convex, and the portion of the second U-shaped element 100 between the parallel arms of the U-shape is concave in order to accommodate a drive wheel for moving sample container carriers 34 along a track.

Figure 6:
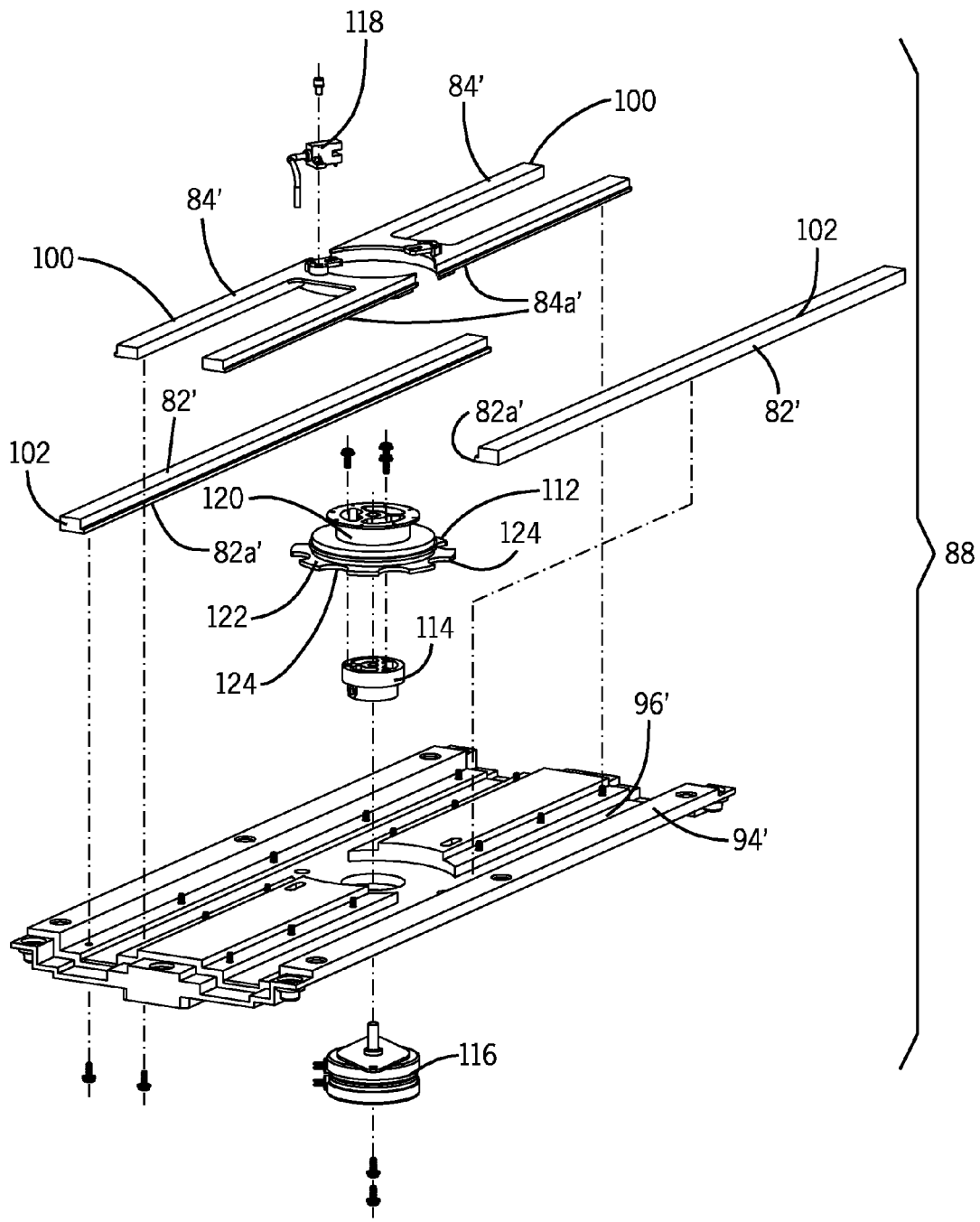
FIG. 6 is an exploded perspective view of a straight section of a drive system for moving carriers for sample tubes.

Referring now to FIG. 6, a straight section 88 comprises a base 94', which contains a recessed area 96' for defining the path upon which sample tube carriers 34 travel. The outer guide rails 82' are formed by elongated elements 102, which are mounted onto the base 94' and fastened to the base 94', typically by means of bolts. The inner guide rails 84' are formed by U-shaped elements 100, which are mounted onto the base 94' and fastened to the base 94', typically by means of bolts. The outer guide rails 82' have ridges 82a' formed on the surface thereof facing the inner guide rails 84', and the inner guide rails 84' have ridges 84a' formed on the surface thereof facing the outer guide rails 82'. The portion of each U-shaped element 100 between the parallel arms of the U-shape is convex in order to accommodate a drive wheel for moving sample container carriers 34 along a track.

Figure 7:
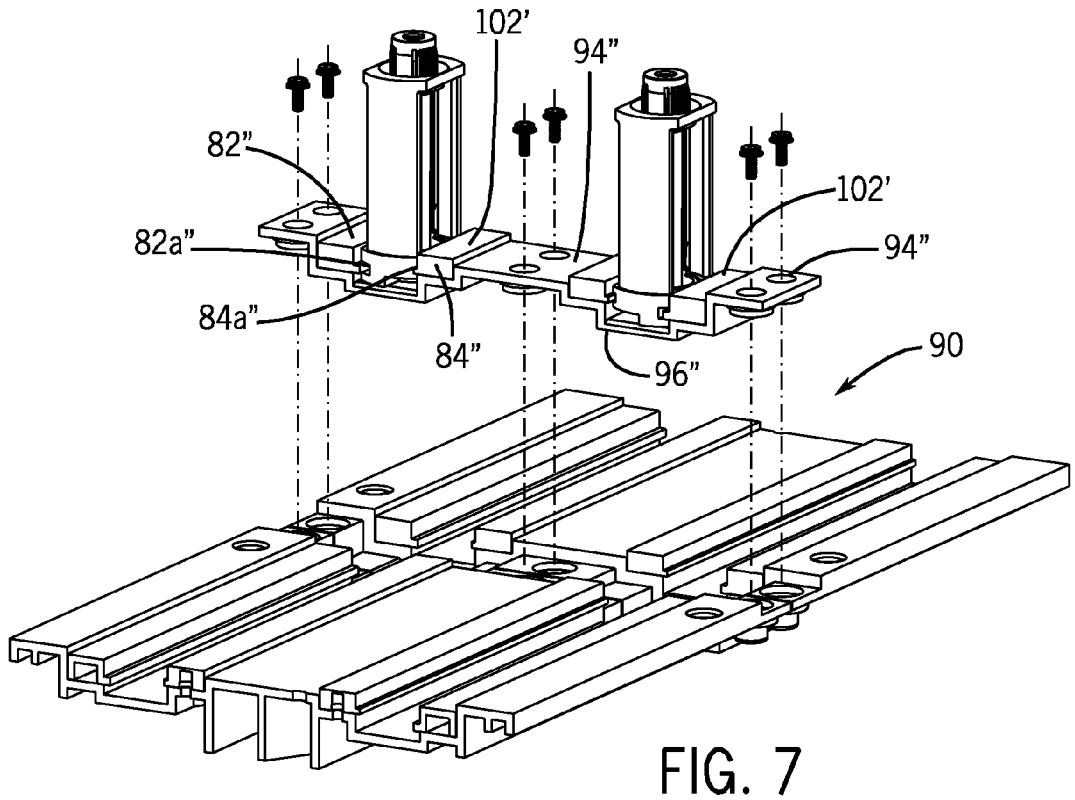
FIG. 7 is an exploded perspective view illustrating how the joining section of the drive system for moving carriers for sample tubes joins two straight sections of a drive system for moving carriers for sample tubes.
Figure 8:
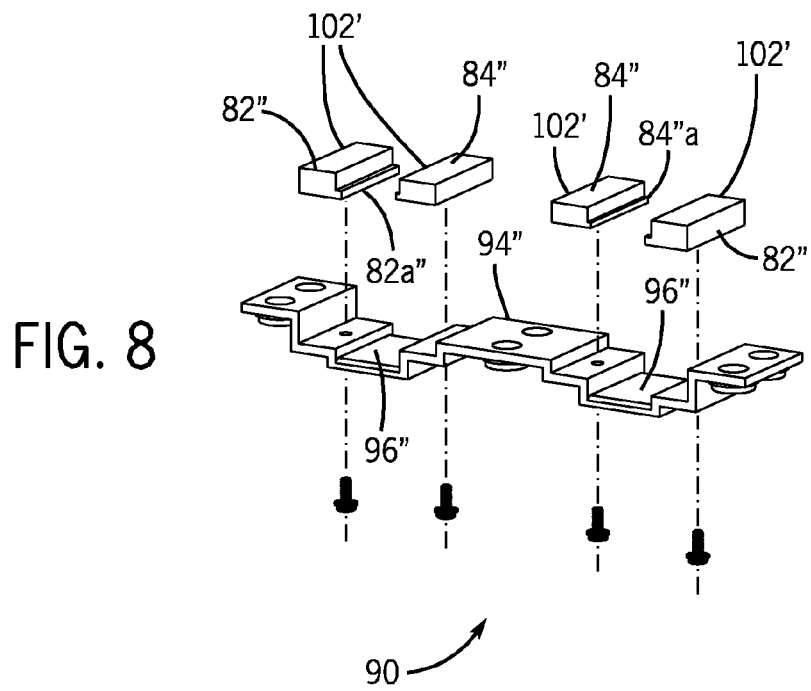
FIG. 8 is an exploded perspective view of a joining section of a drive system for moving carriers for sample tubes.

Referring now to FIGS. 7 and 8, a joining section 90 comprises a base 94", which contains a recessed area 96" for defining the path upon which sample tube carriers 34 travel. The outer guide rails 82" are formed by elongated elements 102', which are mounted onto the base 94" and fastened to the base 94", typically by means of bolts. The inner guide rails 84" are formed by elongated elements 102', which are mounted onto the base 94" and fastened to the base 94", typically by means of bolts. The outer guide rails 82" have ridges 82a" formed on the surface thereof facing the inner guide rails 84", and the inner guide rails 84" have ridges 84a" formed on the surface thereof facing the outer guide rails 82".

Figure 9:
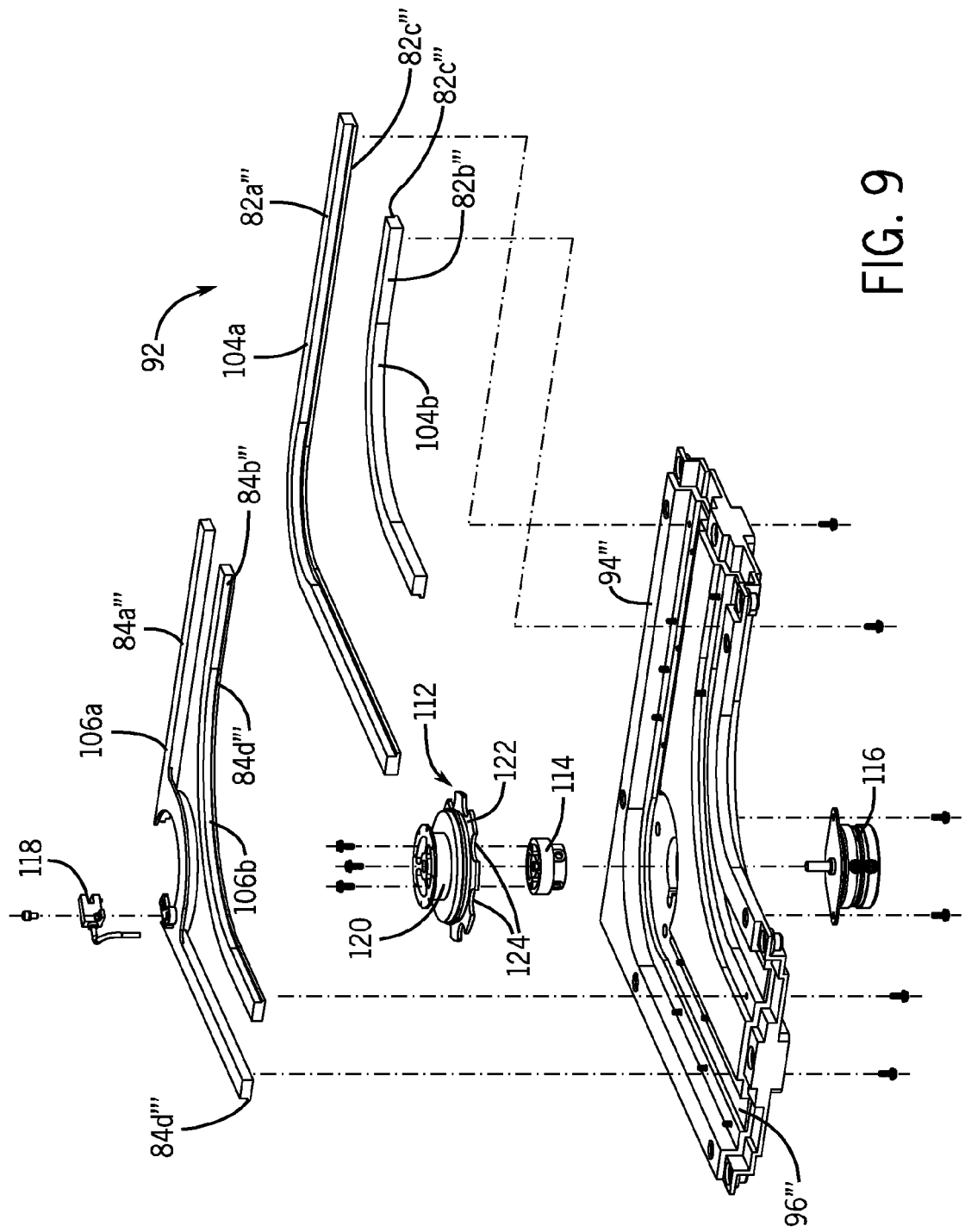
FIG. 9 is an exploded perspective view of a corner section of a drive system for moving carriers for sample tubes.

Corner sections 92 can be used when the configuration of the laboratory requires that the track system turn at an angle, e.g., a right angle, typically on account of space constraints. Other constraints can be presented by the shapes of the automated clinical analyzers employed. Still further constraints can be presented by the customer of the automated clinical analyzer. Referring now to FIG. 9, a corner section 92 comprises a base 94''', which contains a recessed area 96''' for defining the path upon which sample tube carriers 34 travel. The outer guide rails 82a''', 82b''' are formed by curved elements 104a, 104b, which are mounted onto the base 94''' and fastened to the base 94''', typically by means of bolts. The inner guide rails 84a''', 84b''' are formed by curved elements 106a, 106b, which are mounted onto the base 94''' and fastened to the base 94''', typically by means of bolts. The outer guide rails 82a''', 82b''' have ridges 82c''' formed on the surface thereof facing the inner guide rails 84a''', 84b''' and the inner guide rails 84a''', 84b''' have ridges 84d''' formed on the surface thereof facing the outer guide rails 82a''', 82b'''. The outermost outer guide rail 82a''' has a length greater than the innermost outer guide rail 82b''. The outermost inner guide rail 84a'' has a convex portion at the curve in order to accommodate a drive wheel for moving sample container carriers 34 along a track.

The components of the end sections 86, the straight sections 88, the joining sections 90, and the corner sections 92 are preferably made of a molded polymeric material. A representative example of a molded polymeric material suitable for manufacturing the aforementioned end sections 86, the straight sections 88, the joining sections 90, and the corner sections 92 is a 40% glass filled polyphenylene sulfide, commercially available under the trademark RYTON® from Chevron Phillips Chemical Company.

The sample tube carriers 34 are driven along the various tracks described herein by means of a system that comprises a sample tube carrier drive mechanism 110, which comprises a sample tube carrier drive wheel 112, a hub 114 for the sample tube carrier drive wheel 112, and a motor 116 for driving the hub 114, which, in turn, drives the sample tube carrier drive wheel 112. An optical encoder 118 is positioned on an inner guide rail adjacent to the sample tube carrier drive wheel 112. The purpose of the optical encoder 118 is to indicate the position of the sample tube carrier drive wheel 112, and, consequently, the movement of the motor 116. In order for the motor 116 to function properly, the encoder 118 must verify (usually by observation of rotation) the movement of the motor 116. Encoders provide "counts" that can be used to verify and correct stepper motor movements. Encoders verify rotational movement and can be used to correct positional errors.

The sample tube carrier drive wheel 112 comprises a cylindrical body 120 that rests on a base 122. Projecting from the periphery of the base 122 is a plurality of arcuate-shaped recesses 124, each of which serves to loosely grip the base 44 of a sample tube carrier 34. The hub 114 fits into openings in the body 120 and the base 122. A shaft 126 projecting from the motor 116 causes the hub 114 to rotate, thereby causing the sample tube carrier drive wheel 112 to rotate. Such motor-driven drive wheel systems are well-known in the art of conveying objects along a track. The motor 116 can be, for example, a stepper motor. The stepper motor can be a 7.5° stepper motor. A stepper motor is a brushless, synchronous electric motor that can divide a full rotation into a large number of steps. When commutated electronically, the motor's position can be controlled precisely, without any feedback mechanism. See for example, "Stepper motor", [online], [retrieved on 2007-11-28] Retrieved from the Internet: <URL: http://en.wikipedia.org/wiki/Stepper_motor>, incorporated herein by reference. As shown in FIG. 2, a plurality of sample tube carriers 34 can be driven around the track system 32.

The number of sample tube carrier drive mechanisms 110 to be used in any track, track system, or segment of the foregoing, depends upon the length of the track, the track system, or segment of the foregoing, the total weight of the sample tube carriers 34, the total weight of the sample tubes "T" and the contents thereof, and the power ratings of the motors. Generally, as the length of the track, the track system, or segment of the foregoing increases, as the total weight of the sample tube carriers 34 increases, as the total weight of the sample tubes "T" and the contents thereof increases, and as the power ratings of the motors decrease, the number of sample tube carrier drive mechanisms 110 to be used increases.

Figure 14:
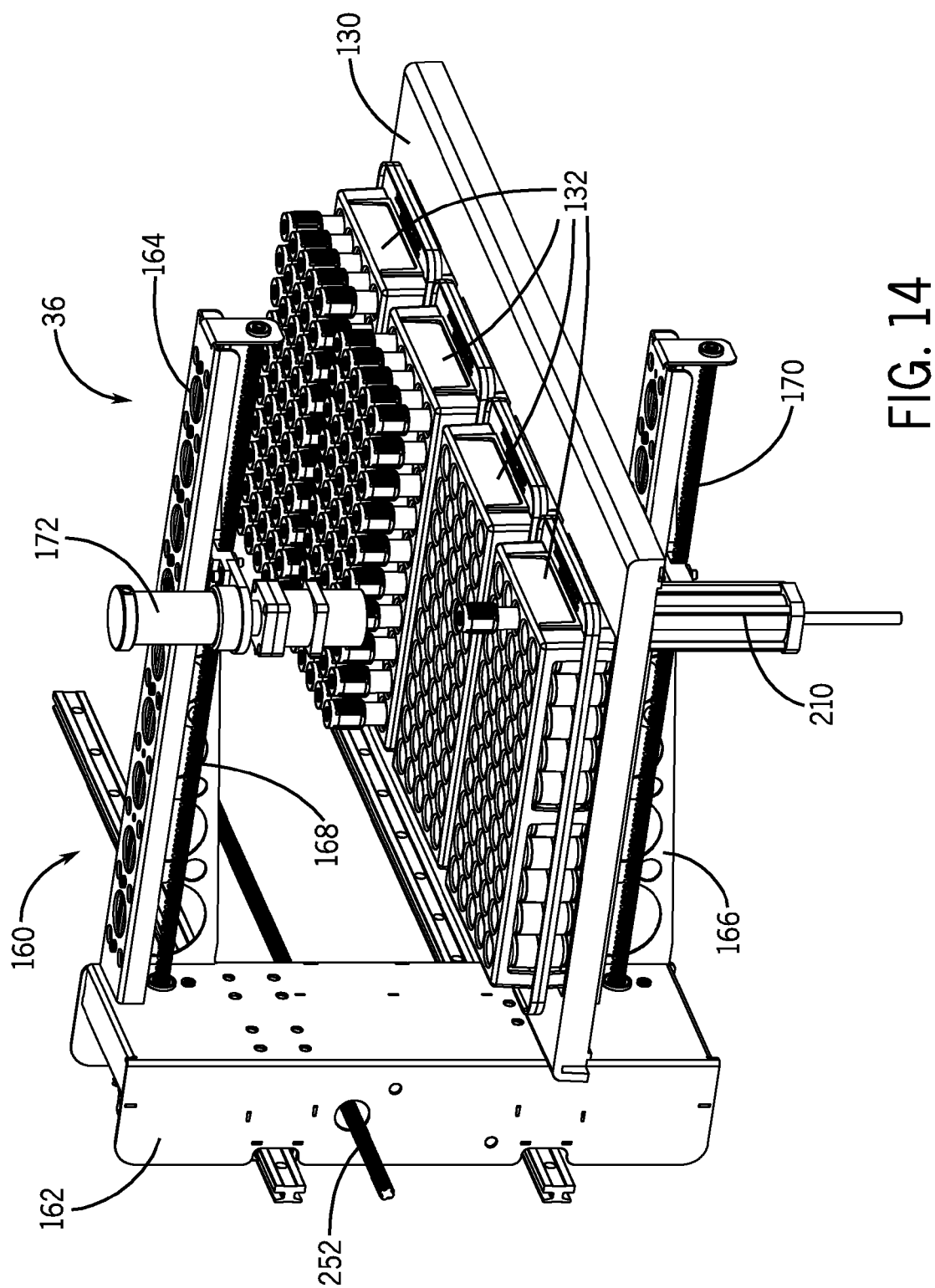
FIG. 14 is a perspective view of the module for selecting sample tubes from the racks for holding the sample tubes and placing the sample tubes onto the module for staging sample tubes and mixing the samples in the sample tubes.

Also shown in FIG. 2 are the module 36 for selecting sample tubes and placing sample tubes and the module 38 for staging sample tubes and mixing samples. These modules 36 and 38 are also shown in FIGS. 14 and 21. The module 36 for selecting sample tubes and placing sample tubes comprises a tray 130, which tray 130 is capable of supporting a plurality of sample tube racks 132. As shown in FIG. 10, each tray 130 is capable of supporting up to four sample tube racks 132. There are numerous configurations involving the tray 130 and the sample tube racks 132. One common configuration involves the use of two sample tube racks 132 for sample tubes "T" to be input to the module 38 for staging sample tubes and mixing samples ("input" sample tube racks 132) and two sample tube racks 132 for sample tubes "T" to be removed from the module 38 for staging sample tubes and mixing samples ("output" sample tube racks 132). Sample tubes "T" containing samples that are to undergo processing are removed from one of the two input sample tube racks 132 and placed in the module 38 for staging sample tubes and mixing samples. After the samples are processed, the sample tubes "T" are removed from the module 38 for staging sample tubes and mixing samples and placed in one of the two output sample tube racks 132. Another common configuration involves the use of four sample tube racks 132 for sample tubes "T" to be input to the module 38 for staging sample tubes and mixing samples ("input" sample tube racks 132) and no sample tube racks 132 for sample tubes "T" to be removed from the module 38 for staging sample tubes and mixing samples ("output" sample tube racks 132). Sample tubes "T" containing samples that are to undergo processing are removed from one of the four input sample tube racks 132 and placed in the module 38 for staging sample tubes and mixing samples. After the samples are processed, the sample tubes "T" are removed from the module 38 for staging sample tubes and mixing samples and placed in the input sample tube rack 132 from which it had previously been removed. As shown in FIG. 10, the tray 130 has a plurality of recessed areas 134 in which the sample tube racks 132 are positioned. The recessed areas 134 have a plurality of openings 136 formed therein. Each sample tube rack 132 comprises a base 138, a cover 140, and a core 142. The base 138 comprises a plurality of sample tube holders 144 having a shape similar to the shape of the lower portion of a sample tube "T". The cover 140 comprises a plurality of sample tube openings 146 having a shape similar to the shape of the exterior wall of a sample tube "T". The core 142 comprises a plurality of sample tube guides 148 having a shape similar to the shape of the exterior wall of a sample tube "T". When the base 138, the cover 140, and the core 142 are properly assembled, the sample tube holders 144, the sample tube openings 146, and the sample tube guides 148 are in register, with the result that the combination of a sample tube holder 144, a sample tube opening 146, and a sample tube guide 148 is capable of supporting a sample tube "T" in a substantially vertical orientation.

Figure 12:
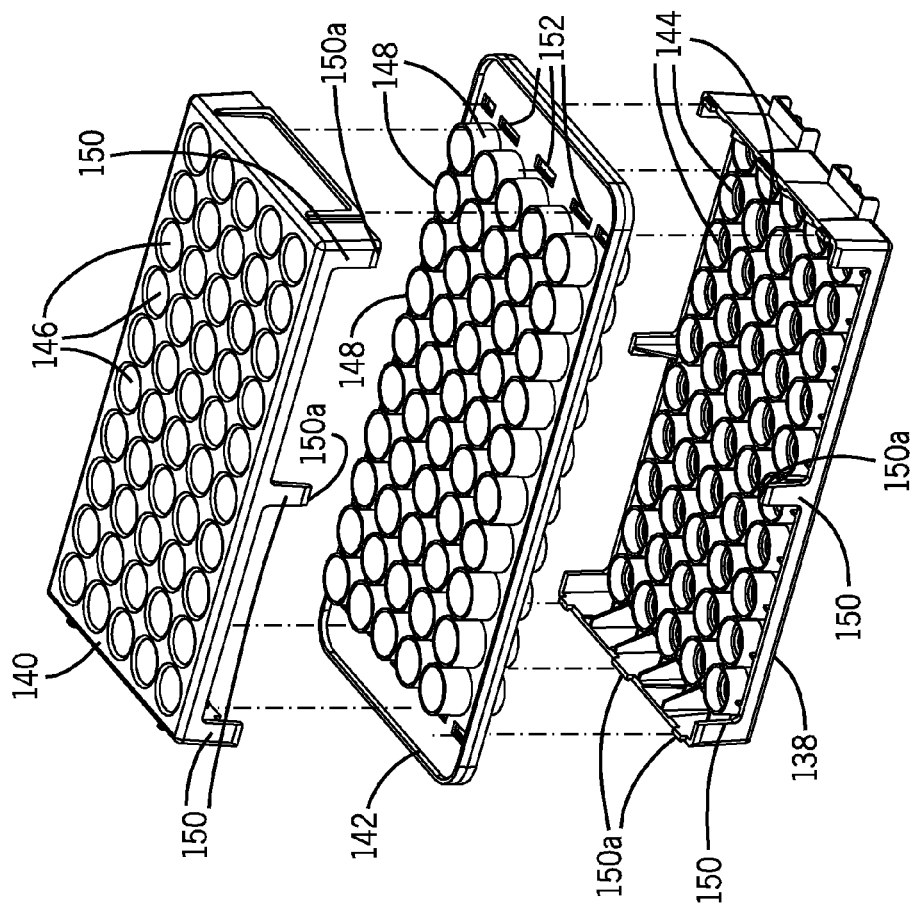
FIG. 12 is an exploded perspective view of the sample tube rack for holding sample tubes shown in FIG. 11.
Figure 11:
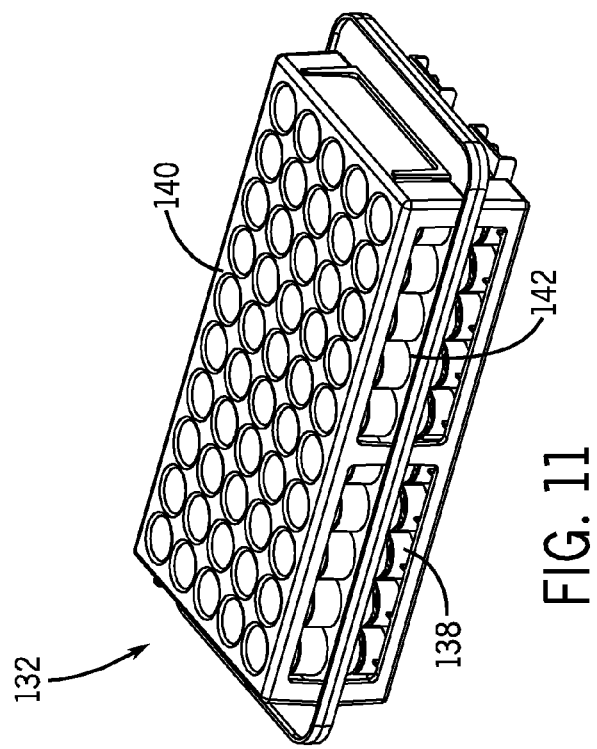
FIG. 11 is a perspective view of a sample tube rack for holding sample tubes.

While there are numerous ways of constructing the sample tube rack 132 shown in FIGS. 11, 12, and 13, a plurality of spacing elements 150 and tabs 150a on the base 138 and the cover 140, and a plurality of slots 152 in the core 142 can be used to provide proper spacing between the base 138, the cover 140, and the core 142 of the sample tube rack 132 and secure locking of the base 138, the cover 140, and the core 142 of the sample tube rack 132.

The tray 130 has a sample tube rack lock 154, which maintains the sample tube rack 132 in the locked position by means of a pair of resilient biasing elements 156a, 156b, such as for example springs. The tray 130 further includes an optical encoder 158, the purpose of which is to indicate when a sample tube rack 132 is present on the tray 130.

As indicated previously, the tray 130 also has a plurality of openings 136 formed in the recessed areas 134 in the major surfaces of the recessed areas 134. Each sample tube holder 144 in the base 138 of the sample tube rack 132 also has an opening (not shown) formed therein at the bottom thereof. The openings 134 in the tray 130 and the openings in the sample tube holder 144 in the base 138 of the sample tube rack 132 are of substantially the same size. The size of the openings 136 and the size of the openings in the in the sample tube holder 144 in the base 138 of the sample tube rack 132 is smaller than the bottom of a sample tube "T", but sufficiently large to enable the passage of a piston therethrough. When the sample tube rack 132 is properly placed on the tray 130, the openings 136 in the tray 130 and the openings in the sample tube holder 144 in the base 138 of the sample tube rack 132 are in register. A piston is capable of passing through the openings (not shown) in the sample tube holder 144 in the base 138 of the sample tube rack 130 and through the openings 136 in the tray 130, whereby the sample tube "T" will be lifted. The usefulness of this lifting feature will be described later.

The trays 130 are preferably made of a molded polymeric material. A representative example of a molded polymeric material suitable for manufacturing the trays 130 is a 40% glass filled polyphenylene sulfide, commercially available under the trademark RYTON® from Chevron Phillips Chemical Company. The components of the sample tube rack 132, i.e., the base 138, the cover 140, and the core 142, are preferably made of a molded polymeric material.

The module 36 for selecting sample tubes and placing sample tubes further comprises a robotic system 160 that is capable of removing a sample tube "T" from a sample tube rack 132 and placing the removed sample tube "T" into a sample tube carrier 34 in the module 38 for staging sample tubes and mixing samples. The robotic system 160 is also capable of removing a sample tube "T" from the track system 32 and placing the sample tube "T" onto the module 36 for selecting sample tubes and placing sample tubes, and vice versa. The robotic system 160 is further capable of removing a sample tube "T" from the track system 32 and placing the sample tube "T" onto the module 38 for staging sample tubes and mixing samples, and vice versa.

Figure 15:
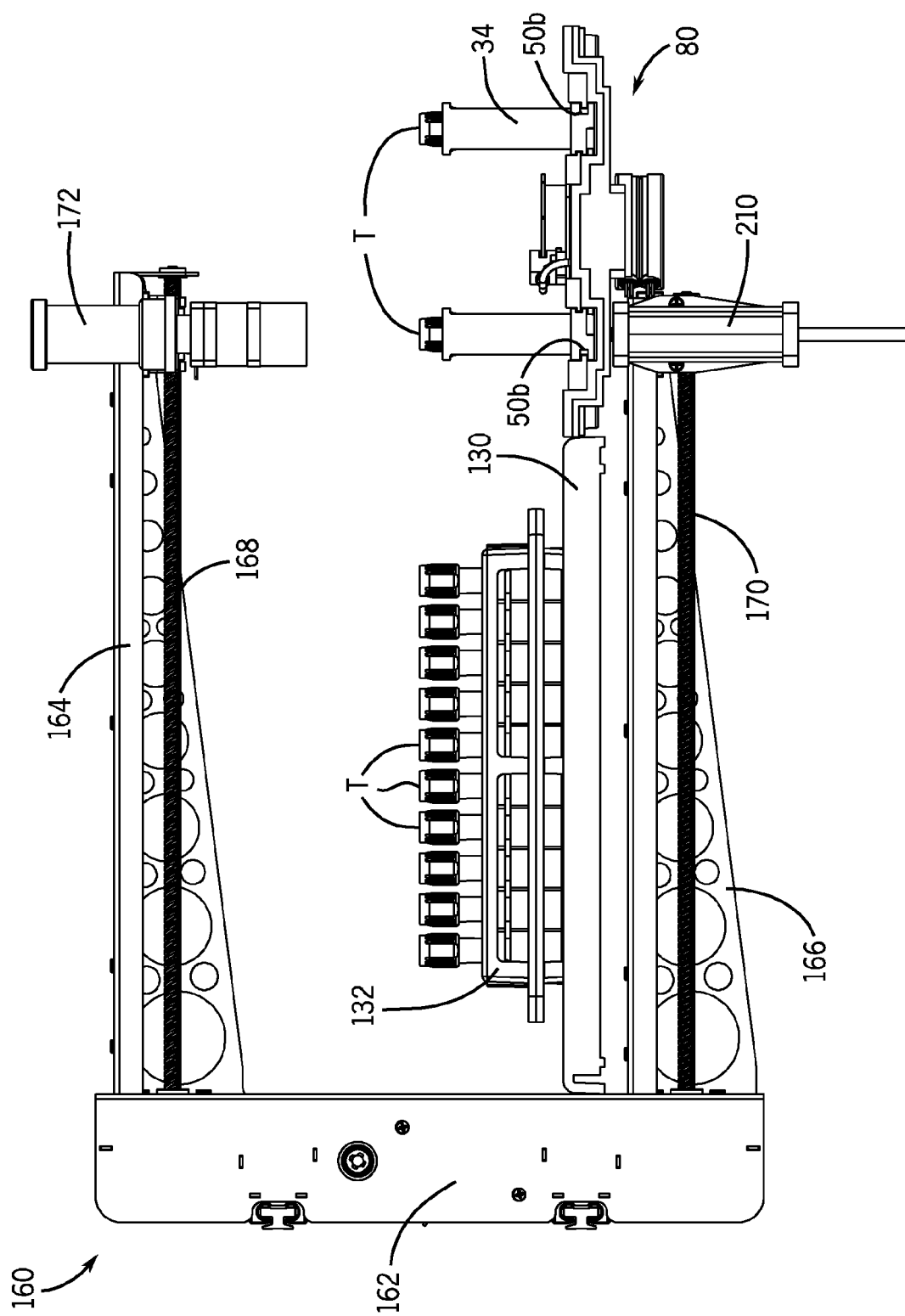
FIG. 15 is a side view in elevation of a robotic system for selecting sample tubes from the racks for holding the sample tubes and placing the sample tubes onto the module for staging sample tubes and mixing the samples in the sample tubes.

Referring now to FIGS. 14 and 15, the robotic system 160 comprises an upright element 162. From the upright element 162 project both an upper elongated horizontal support element 164 and a lower elongated horizontal support element 166. The upper elongated horizontal support element 164 and the upright element 162 support a first lead screw 168. The lower elongated horizontal support element 166 and the upright element 162 support a second lead screw 170. The first lead screw 168 and the second lead screw 170 are typically made out of stainless steel. Lead screws that can be adapted for use herein, and the design considerations for such lead screws, are described in greater detail in ACME & LEAD SCREW ASSEMBLY GLOSSARY AND TECHNICAL DATA, [online], [retrieved on 2007-11-25] Retrieved from the Internet: <URL: http://www.nookindustries.com/Acme/AcmeGlossary.cfm>, incorporated herein by reference.

Along the shaft of the first lead screw 168 can travel a sample tube receiver 172. Referring now to FIG. 19, the sample tube receiver 172 comprises a body 174, which body 174 surrounds a flexible, inflatable bladder 176. The flexible, inflatable bladder 176 can be inflated by air supplied by a source of air (not shown). A stretcher 178 is also provided for the flexible, inflatable bladder 176. The flexible, inflatable bladder 176 can be made of rubber. Located above the flexible, inflatable bladder 176 is a cap 180. The cap 180 has an opening 182 through which is placed (journaled) a piston 184. Located above the cap 180 is a base 186 for an air cylinder, above which base 186 is a body 188. The base 186 also has an opening 190 that is in register with the opening 182 in the cap 180. The piston 184 is disposed in the body 188 in such a manner that the shaft 192 of the piston 184 extends through the opening 182 in the cap 180 and the opening 190 in the base 186. Bearing(s) 194 and seal(s) 196a, 196b, typically O-ring seals, can be positioned within the sample tube receiver 172, as required. The base 186 is attached to a carriage assembly 198, which is capable of moving along the shaft of the first lead screw 168 when actuated by a signal from a computer and powered by a suitable drive system. The carriage assembly 198 comprises a lead screw nut 198a, a linear slide 198b, a mounting bracket 198c, and miscellaneous hardware.

The shaft of the first lead screw 168 is capable of being rotated about its major axis by means of a pulley or drive wheel 200. Referring now to FIGS. 16 and 18, the pulley or drive wheel 200 can be caused to rotate about its axis by means of a drive belt 202, which drive belt 202 is driven by a pulley or drive wheel 204. The pulley or drive wheel 204 can be driven by a motor 206, which motor 206 can be a stepper motor. Other types of motors suitable for driving lead screws include servo motors, AC gear motors, and DC gear motors. The motor 206 is actuated by software.

Representative examples of materials that are suitable for constructing the major components of the sample tube receiver 172 are set forth in TABLE 1.

TABLE 1

| Component | Material of construction |
| --- | --- |
| Body 188 | Aluminum 6061-T6 |
| Bladder 176 | Neoprene rubber |
| Stretcher 178 | Aluminum tubing |
| Cap 180 | Aluminum 6061-T6 |

Along the shaft of the second lead screw 170 can travel a sample tube lifter 210. Referring now to FIG. 20, the sample tube lifter 210 comprises a base 212 having an opening 214 therein, a plurality of stays 216a, 216b, 216c, and 216d, a body 218, and a cap 220 having opening 222 therein. Disposed within the body 218 is a piston 224. One end 224a of the piston 224 can move through the opening 214 in the base 212. The other end 224b of the piston 224 can move through the opening 222 in the cap 220. The piston 224 has a seal 226 positioned approximately at the mid-point thereof for the purpose of preventing air from leaking between the piston 224 and the body 218. Bearing(s) 228a, 228b and seal(s) 230a, 230b, 230c, 230d, typically O-ring seals, can be positioned within the sample tube lifter 210, as required. Representative examples of materials that are suitable for constructing the major components of the sample tube lifter 210 are set forth in TABLE 2.

TABLE 2

| Component | Material of construction |
|---|---|
| Base 212 | Aluminum 6061-T6 |
| Stay 216a, 216b, 216c, 216d | Aluminum 6061-T6 |
| Cylindrical body | Aluminum tubing |
| Piston 224 | Stainless steel |
| Cap 220 | Aluminum 6061-T6 |

A system for detecting the sample tube "T" can be included with the sample tube receiver 172 and the sample tube lifter 210. A typical system for detecting whether a sample tube "T" is between the sample tube receiver 172 and the sample tube lifter 210 comprises a photodetector 232 and a light-emitting diode 234. The system for detecting the presence of a sample tube "T" indicates whether a sample tube "T" is between the sample tube receiver 172 and the sample tube lifter 210. If a sample tube "T" is within the sample tube receiver 172, the light beam between the light-emitting diode 234 and the phoptodetector 232 will be blocked, thereby indicating the presence of a sample tube "T" in the sample tube receiver 172. If a sample tube "T" is not within the sample tube receiver 172, the light beam between the light-emitting diode 234 and the photodetector 232 will not be blocked, thereby indicating the absence of a sample tube "T" in the sample tube receiver 172. The cap 220 is attached to a carriage assembly 238, which is capable of moving along the shaft of the second lead screw 170 when actuated by a signal from a computer and powered by a suitable drive system. The carriage assembly 238 comprises a lead screw nut 238a, a linear slide 238b, a mounting bracket 238c, and miscellaneous hardware.

The shaft of the second lead screw 170 is capable of being rotated about its major axis by means of a pulley or drive wheel 200'. Referring again to FIG. 16, the pulley or drive wheel 200' can be caused to rotate about its axis by means of a drive belt (not shown), which drive belt is driven by a pulley or drive wheel (not shown). The pulley or drive wheel can be driven by a motor 206', which motor 206' can be a stepper motor. Other types of motors suitable for driving lead screws include servo motors, AC gear motors, and DC gear motors. The motor 206' is actuated by software. There is no drawing to illustrate an exploded view of the assembly for turning the second lead screw 170, because the assembly for driving the second lead screw 170 would be expected to be identical to or substantially similar to the drawing shown in FIG. 18.

Referring again to FIG. 16, the upright element 162 is attached to a carriage assembly 250, which is capable of moving along the shaft of a third lead screw 252 when actuated by a signal from a computer and powered by a suitable drive system. The carriage assembly 250 comprises a lead screw nut (not shown), a linear slide (not shown), a mounting bracket (not shown), and miscellaneous hardware.

The shaft of the third lead screw 252 is capable of being rotated about its major axis by means of a pulley or drive wheel 254. Referring to FIG. 17, the pulley or drive wheel 254 can be caused to rotate about its axis by means of a drive belt 256, which drive belt 256 is driven by a pulley or drive wheel 258. The pulley or drive wheel 258 can be driven by a motor 260, which motor 260 can be a stepper motor. Other types of motors suitable for driving lead screws include servo motors, AC gear motors, and DC gear motors. The motor 260 is actuated by software.

Referring now to FIGS. 23, 24, 25, and 26, the module 38 for staging sample tubes and mixing samples comprises a track 270 that can convey a plurality of sample tube carriers 34. The sample tube carriers 34 are conveyed along the track 270 to a mixing drum 272. The track 270 is bounded by an outer guide rail 274 and an inner guide rail 276. The sample tube carriers 34 are driven by means of a system that comprises a sample tube carrier drive mechanism 280, which comprises a sample tube carrier drive wheel 282, a hub 284 for the sample tube carrier drive wheel 282, and a motor (not shown), typically a stepper motor. The motor is in register with the sample tube carrier drive wheel 282 and the hub 284 for the sample tube carrier drive wheel 282 and is positioned directly below the sample tube carrier drive wheel 282 and the hub 284 for the sample tube carrier drive wheel 282.

As shown in FIGS. 23, 24, 25, and 26, the mixing drum 272 comprises a cylindrical element 288. A representative example of a material that is suitable for constructing the mixing drum 272 is 40% glass filled polyphenylene sulfide, commercially available under the trademark RYTON® from Chevron Phillips Chemical Company.

The central axis of the cylindrical element 288 runs generally parallel to the path of travel of the sample tube containers 34 immediately preceding the cylindrical element 288 and immediately following the cylindrical element 288. As used herein, the expression "central axis" means the imaginary line through the centers of and perpendicular to the circular ends of the cylindrical element 288. The cylindrical element 288 comprises a left half 290 and a right half 292. In the left half 290 of the cylindrical element 288 is an opening 294 that runs from a first segment on the periphery of the left half 290 of the cylindrical element 288 to a second segment on the periphery of the left half 290 of the cylindrical element 288, each point of the second segment on the periphery of the left half 290 the cylindrical element 288 being 180° offset from a corresponding point of the first segment on the periphery of the left half 290 the cylindrical element 288. Likewise, in the right half 292 of the cylindrical element 288 is an opening 296 that runs from a first segment on the periphery of the right half 292 of the cylindrical element 288 to a second segment on the periphery of the right half 292 of the cylindrical element 288, each point of the second segment on the periphery of the right half 292 of the cylindrical element 288 being 180° offset from a corresponding point of the first segment on the periphery of the right half 292 the cylindrical element 288. It is preferred that the opening 296 be in register with the opening 294. The mixing drum 272 can be formed of a molded polymeric material. A representative example of a polymeric material suitable for preparing the mixing drum 272 is 40% glass filled polyphenylene sulfide, commercially available under the trademark RYTON® from Chevron Phillips Chemical Company. The mixing drum 272 is of a size sufficient to accommodate at least one sample tube carrier 34 containing a sample tube "T".

The exterior of the left half 290 of the cylindrical element 288 has a recess 298 formed at the leftmost end of the cylindrical element 288. The recess 298 completely encircles the leftmost end of the periphery of the left half 290 of the cylindrical element 288. Similarly, the exterior of the right half 292 of the cylindrical element 288 has a recess 300 formed at the rightmost end of the cylindrical element 288. The recess 300 completely encircles the rightmost end of the periphery of the right half 292 of the cylindrical element 288. The cylindrical element 288 is supported by means of a pair of fixed retaining arms 302, 304 and a pair of spring-biased retaining arms 306, 308. The fixed retaining arms 302, 304 and the spring-biased retaining arms 306, 308 are provided with rollers 310. The rollers 310 are guided by the recess 298 formed in the left half 290 of the cylindrical element 288 and by the recess 300 formed in the right half 292 of the cylindrical element 288. In order to drive the cylindrical element 288 about its central axis, i.e., the imaginary line through the center of and perpendicular to the circular ends of the cylindrical element 288, a toothed wheel 312 is formed about the circumference of the cylindrical element 288, preferably midway between the recess 298 of the cylindrical element 288 and the recess 300 of the cylindrical element 288. The teeth of the toothed wheel 312 are engaged with the teeth of a drive gear 314. When the drive gear 314 is rotated, the cylindrical element 288 is caused to rotate. The drive gear 314 is driven by a motor 316, which motor 316 can be a stepper motor. It is preferred that the mixing drum 272 be capable of rotating from about five (5) to ten (10) revolutions per minute. It is also preferred that the direction of rotation of the mixing drum 272 be alternated, i.e., from clockwise to counter-clockwise, e.g., from 90° to 180° clockwise followed by from 90° to 180° counter-clockwise, during the mixing cycle to simulate mixing by hand or rocker. The speed of rotation must not be so great that the solid components of the sample, e.g., red blood cells, separates from the liquid components of the sample, e.g., plasma. The openings 294, 296 in the mixing drum 272 must be sufficiently large and shaped in such a manner that a sample tube carrier 34 along with a sample tube "T" be able to pass through the openings 294, 296.

In order for the automated clinical analyzer to obtain access to the contents of a sample tube "T", the cap "C" of the sample tube "T" must be pierced. The module 38 for staging sample tubes and mixing samples includes a piercing assembly 320. See FIGS. 22, 26, 27A, 27B, 27C, and 27D. The piercing assembly 320 comprises a piercing element 322, which is held in position by a supporting structure 324. The piercing assembly 320 is alternately referred to herein as a venting assembly, for the reason that piercing the cap "C" of a sample tube "T" also results in venting gases from the sample tube "T". As shown in FIGS. 22, 26, 27A, 27B, 27C, and 27D, the supporting structure 324 comprises two mounting posts 326 and 328, which support a cross member 330. Positioned below the cross member 330 is a cap-piercing mechanism 332. The cap-piercing mechanism 332 comprises an upper portion 334 and a lower portion 336. The upper portion 334 comprises a centering cone 338, which fits over the cap "C" of a sample tube "T", a body 340, a resiliently biased piercing element 322 located with the body 340, a resilient biasing element 342, e.g., a spring, located within the body 340. The purpose of the centering cone 338 is to aligned the cap "C" of the sample tube "T" with the piercing element 322. The purpose of the resilient biasing element 342 is to eject the sample tube from the upper portion 334 of the cap-piercing mechanism 332 after the cap "C" has been pierced. The lower portion 336 comprises a body 346, a piston 348, and an air cylinder 350. The body 346 is typically cylindrical in shape. The piston 348 comprises an elongated shaft 352 having a head 354 at the lower end of the elongated shaft 352. The purpose of piston 348 is to raise the sample tube "T" in order to pierce the cap "C". The purpose of the air cylinder 350 is to provide air in order to extend the piston 348 vertically in the upward direction.

Representative examples of materials that are suitable for constructing the major components of the piercing assembly 320 are set forth in TABLE 3.

TABLE 3

| Component | Material of construction |
| --- | --- |
| Body 340 | Molded from 40% glass filled polyphenylene sulfide, commercially available under the trademark RYTON ® from Chevron Phillips Chemical Company. |
| Wash block and centering cone 338 | Injection molded from high density polyethylene plastic |
| Resilient biasing element 342 | Stainless steel spring |
| Piercing element 322 | Stainless steel needle |

Figure 23:
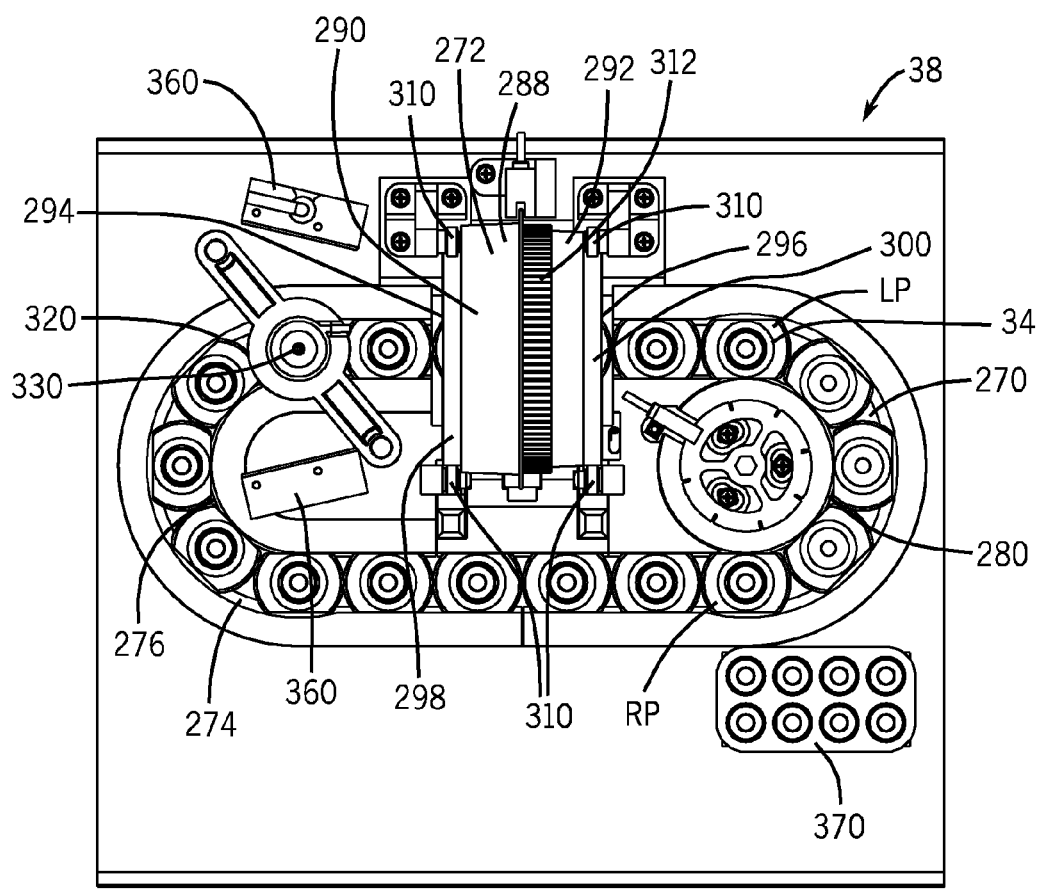
FIG. 23 is a top plan view of the module for staging sample tubes and mixing the samples in the sample tubes shown in FIG. 22.

The module 38 for staging sample tubes and mixing samples further comprises at least one reader 360 for reading information associated with the sample tube "T". As shown in FIG. 23, the at least one reader 360 comprises two barcode readers. Two barcode readers are used in order to ensure that the entire barcode label will be read. However, it is contemplated that radio frequency identification reader(s) can be used in place of barcode reader(s), so long as the label is a radio frequency identification tag.

An auxiliary sample tube rack 370 is positioned on the module 38 for staging sample tubes and mixing samples. This auxiliary sample tube rack 370 can be used for holding control samples for calibration of instruments, holding stat samples for immediate processing, and for retrieving samples for additional processing, such as, for example, retesting of the sample and the making of slides. Samples for processing are removed directly from the auxiliary sample tube rack 370 and placed in the sample tube loading position "LP" of the module 38 for staging sample tubes and mixing samples. After the samples in these sample tubes are processed, the sample tubes are removed from sample tube removal position "RP" of the module 38 for staging sample tubes and mixing samples and placed back into the auxiliary sample tube rack 370. Samples requiring additional processing can be diverted from returning to the sample tube racks 132 and transferred to the auxiliary sample tube rack 370 for ease of retrieval.

Operation

Referring now to FIG. 2, a plurality of sample tube carriers 34 containing sample tubes "T" can be loaded by an operator onto the track system 32. The track system 32 enables the sample tube carriers 34 to move around the track system 32 by means of power supplied by one or more stepper motors.

Sample tubes "T" can be removed from the sample tube carriers 34 on the track system 32 and placed into the sample tube racks 132 on the module 36 for selecting sample tubes and placing sample tubes by the robotic system 160. Sample tubes "T" can also be removed from the module 36 for selecting sample tubes and placing sample tubes and placed into sample tube carriers 34 on the track system 32 by the robotic system 160. Sample tubes "T" can be removed from the sample tube carriers 34 on the track system 32 and placed into sample tube carriers 34 on the track 270 of the module 38 for staging sample tubes and mixing samples by the robotic system 160. Samples tubes "T" can also be removed from the track 270 on the module 38 for staging sample tubes and mixing samples and placed into sample tube carriers 34 on the track system 32 by the robotic system 160.

More typically, the sample tubes "T" can be removed from the sample tube racks 132 of the module 36 for selecting sample tubes and placing sample tubes and placed into sample tube carriers 34 on the track 270 of the module 38 for staging sample tubes and mixing samples by the robotic system 160. Alternatively, the sample tubes "T" can be removed from the sample tube carriers 34 on the track 270 of the module 38 for staging sample tubes and mixing samples and placed into the sample tube racks 132 in the module 36 for selecting sample tubes and placing sample tubes by the robotic system 160.

Figure 21F:
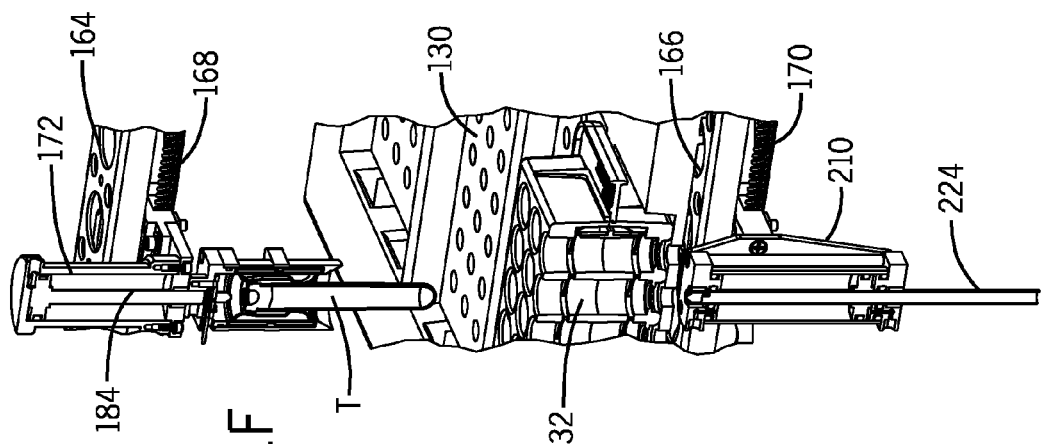
Figure 21E:
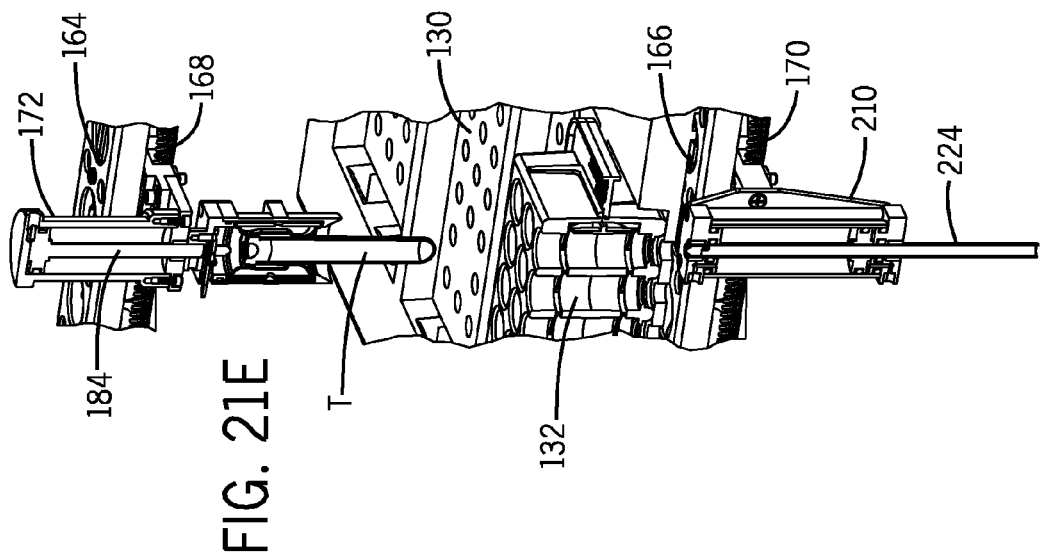
Figure 21D:
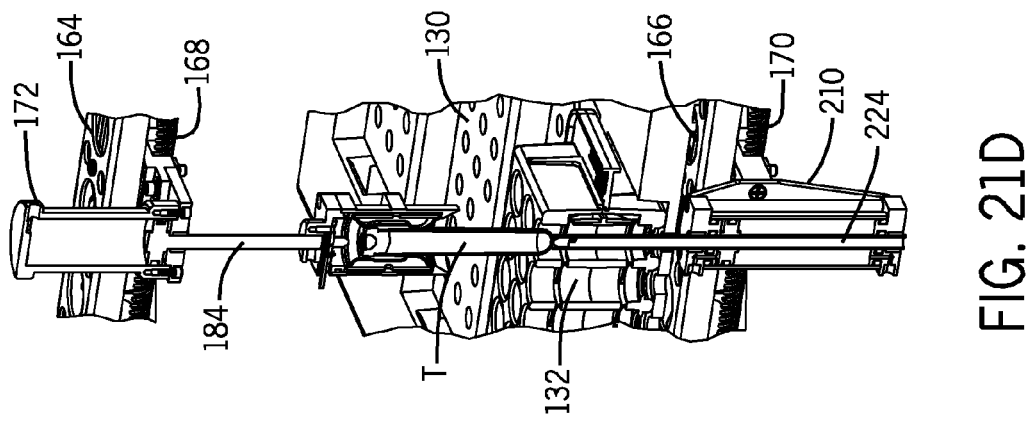
Figure 21I:
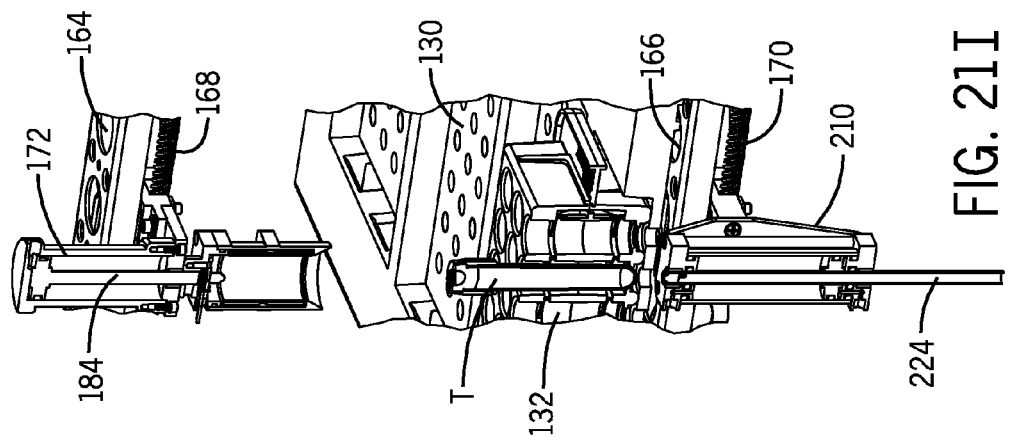
Figure 21H:
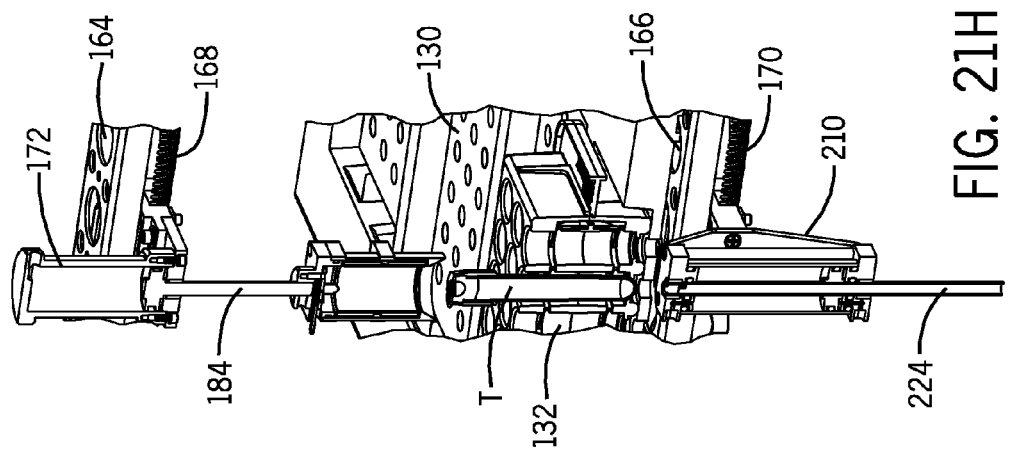
Figure 21G:
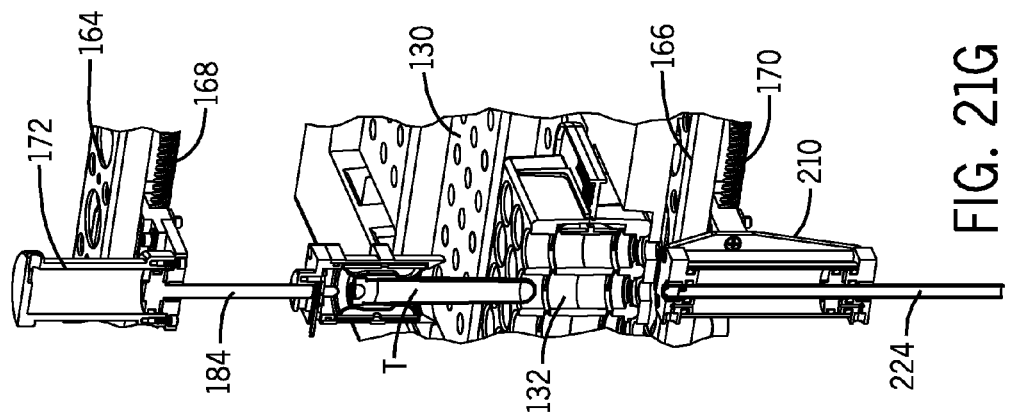
Figure 22:
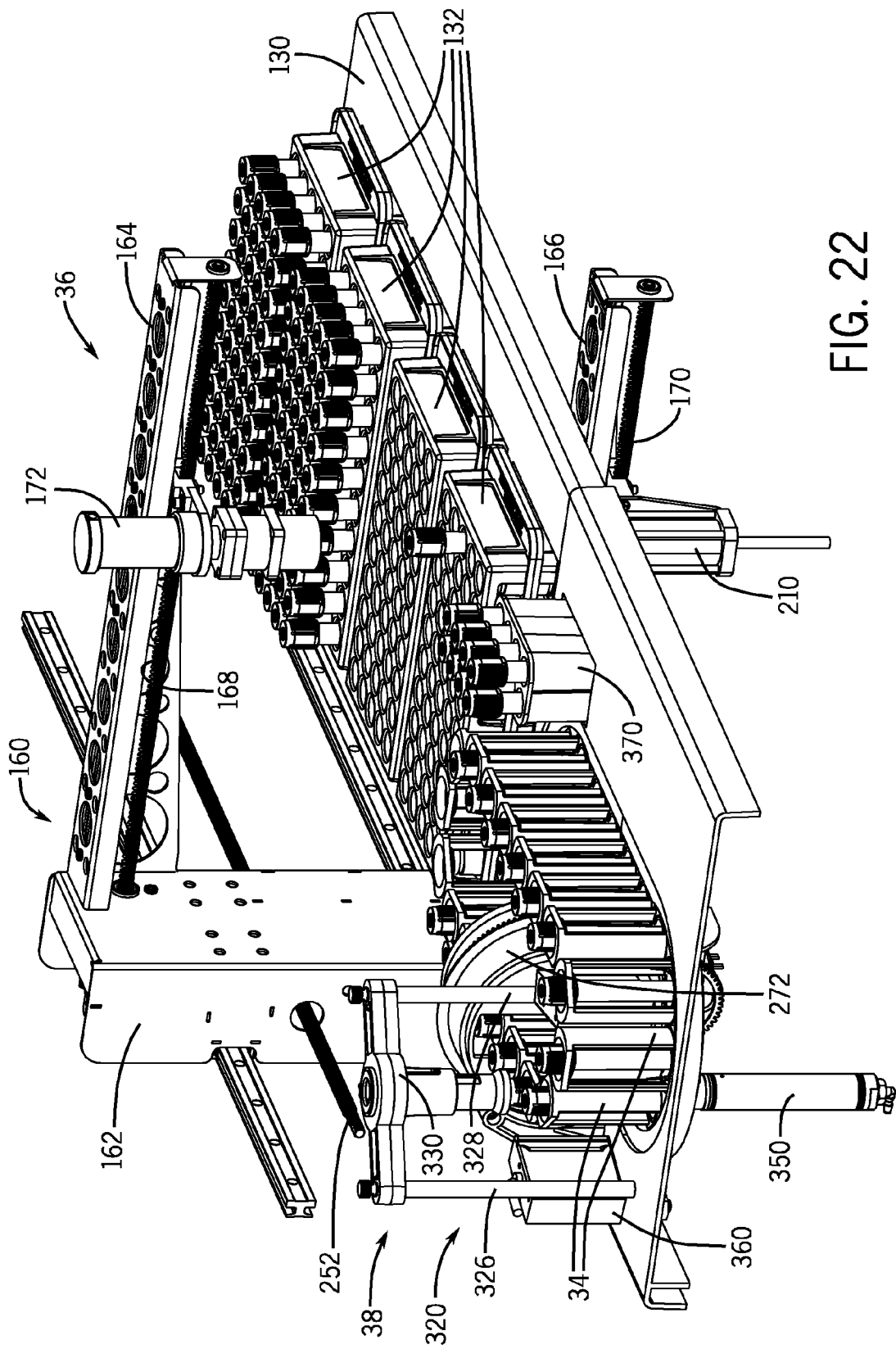
FIG. 22 is a perspective view, greatly enlarged, of the module for staging sample tubes and mixing the samples in the sample tubes and the module for selecting sample tubes from the racks for holding the sample tubes and placing the sample tubes onto the module for staging sample tubes and mixing the samples in the sample tubes, as previously shown in FIG. 14.

Turning now to more specific details of the foregoing operations, FIGS. 21A, 21B, 21C, 21D, 21E, 21F, 21G, 21H, and 21I illustrate the basic steps that are carried out to remove a sample tube "T" from either a first sample tube carrier 34 or from a sample tube rack 132 in order to allow the transfer of the sample tube "T" to a second sample tube carrier 34. Sample tube racks 132 are located on the module 36 for selecting sample tubes and placing sample tubes. As indicated previously, sample tube carriers 34 are used on the track system 32 and on the track 270 of the module 38 for staging sample tubes and mixing samples. Referring now to FIG. 21A, the sample tube receiver 172 and the sample tube lifter 210 are moved to a specific location of a sample tube "T". The sample tube rack 132 is positioned above the tray 130. Referring now to FIG. 21B, the sample tube receiver 172 is extended vertically in a downward direction, by means of the piston 184, which is actuated by air from an air supply (not shown), over and very close to the sample tube "T". Referring now to FIG. 21C, the sample tube lifter 210 extends vertically in an upward direction, and the piston 224 pushes the sample tube "T" upwardly to an extent sufficient for the upper 25% to 50% of the sample tube "T" to enter the body 174 of the sample tube receiver 172. Referring now to FIG. 21D, the flexible, inflatable bladder 176 of the sample tube receiver 172 is inflated, thereby enabling the body 174 of the sample tube receiver 172 to securely grip the sample tube "T". Referring now to FIG. 21E, the sample tube receiver 172 is retracted. The sample tube lifter 210 is also retracted. Referring now to FIG. 21F, the sample tube receiver 172 is moved to the next location, such as for example, a sample tube carrier 34 on the module 38 for staging sample tubes and mixing sample. The sample tube lifter 210 is also moved to the next location, such as for example, a sample tube carrier 34 on the module 38 for staging sample tubes and mixing sample. Referring now to FIG. 21G, the sample tube receiver 172 is extended vertically in a downward direction. Referring now to FIG. 21H, the flexible, inflatable bladder 176 is deflated, thereby releasing the sample tube "T", such as, for example, into a sample tube carrier 34 on the module 38 for staging sample tubes and mixing samples. Referring now to FIG. 21I, the sample tube receiver 172 is then retracted.

FIG. 23 can be used to illustrate the path followed by a sample tube carrier 34 holding a sample tube "T". The path commences at the point at which a sample tube "T" is placed in a sample tube carrier 34 on the track 270 and terminates at the point at which a sample tube "T" is removed from the track 270. Referring now to FIG. 23, the sample tube "T" is placed in a sample tube carrier 34 on the track 270 at the sample tube loading position "LP". The sample tube loading position "LP" is selected to be adjacent to the sample tube carrier drive mechanism, for the reason that the motor 116 stabilizes the sample tube carrier 34. At this position, slippage of the sample tube carrier 34 is less likely to occur than at other positions on the track 270. It should be noted that the recessed area of the track 270 at this position must have an opening (not shown) formed therein, so that the piston 224 of the sample tube lifter 210 can pass through this opening and into the opening 52 in the base 44 of the sample tube carrier 34. The presence of this opening enables the sample tube receiver 172 and the sample tube lifter 210 to carry out the procedure described previously in conjunction with FIGS. 21A, 21B, 21C, 21D, 21E, 21F, 21G, 21H, and 21I.

Figure 24:
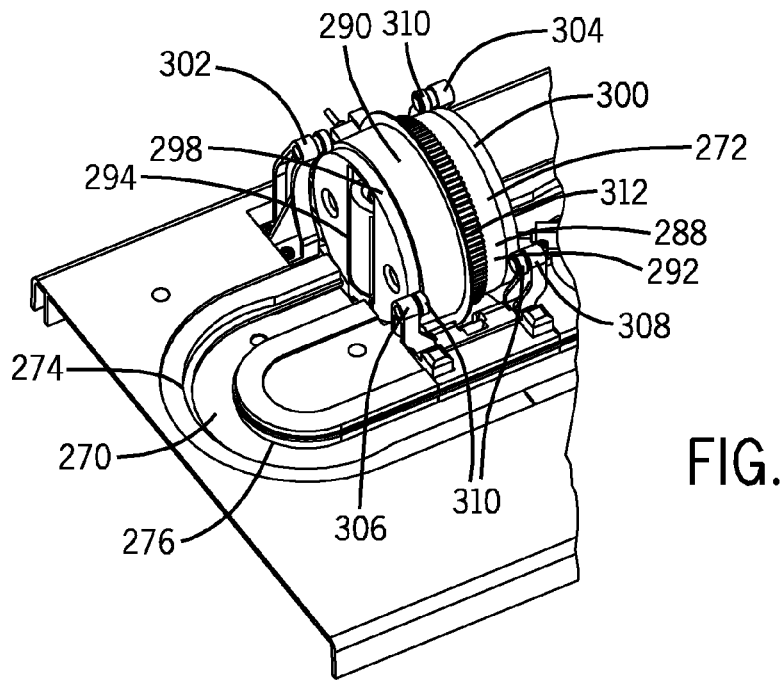
FIG. 24 is a partial perspective view of the mixing drum of the module for staging sample tubes and mixing the samples in the sample tubes shown in FIGS. 22 and 23.
Figure 25:
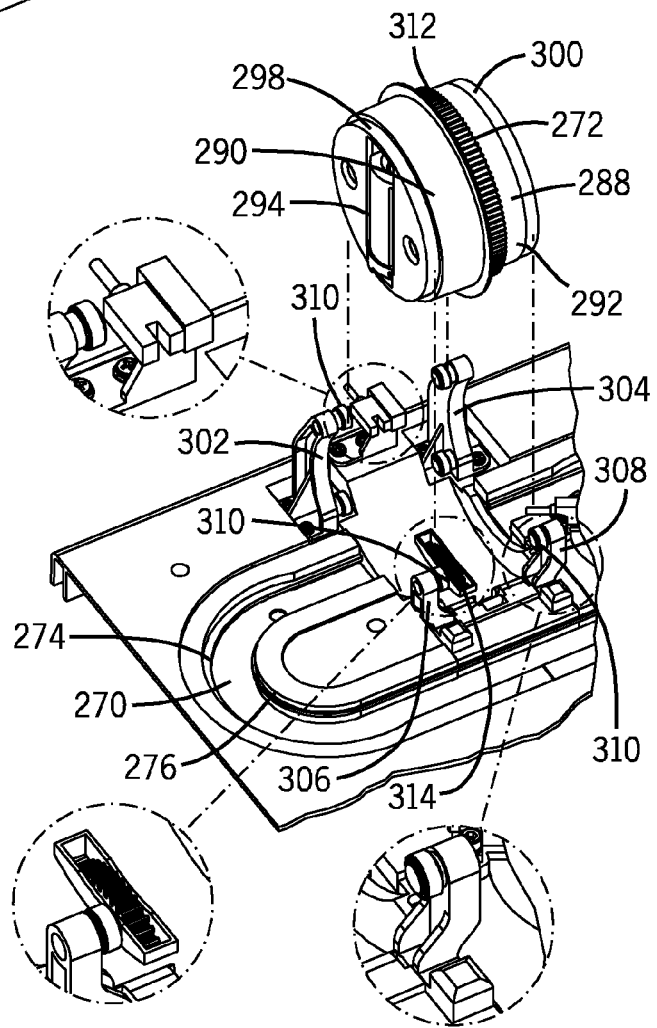
FIG. 25 is an exploded perspective view of the mixing drum of the module for staging sample tubes and mixing the samples in the sample tubes shown in FIGS. 22, 23, and 24.
Figure 26:
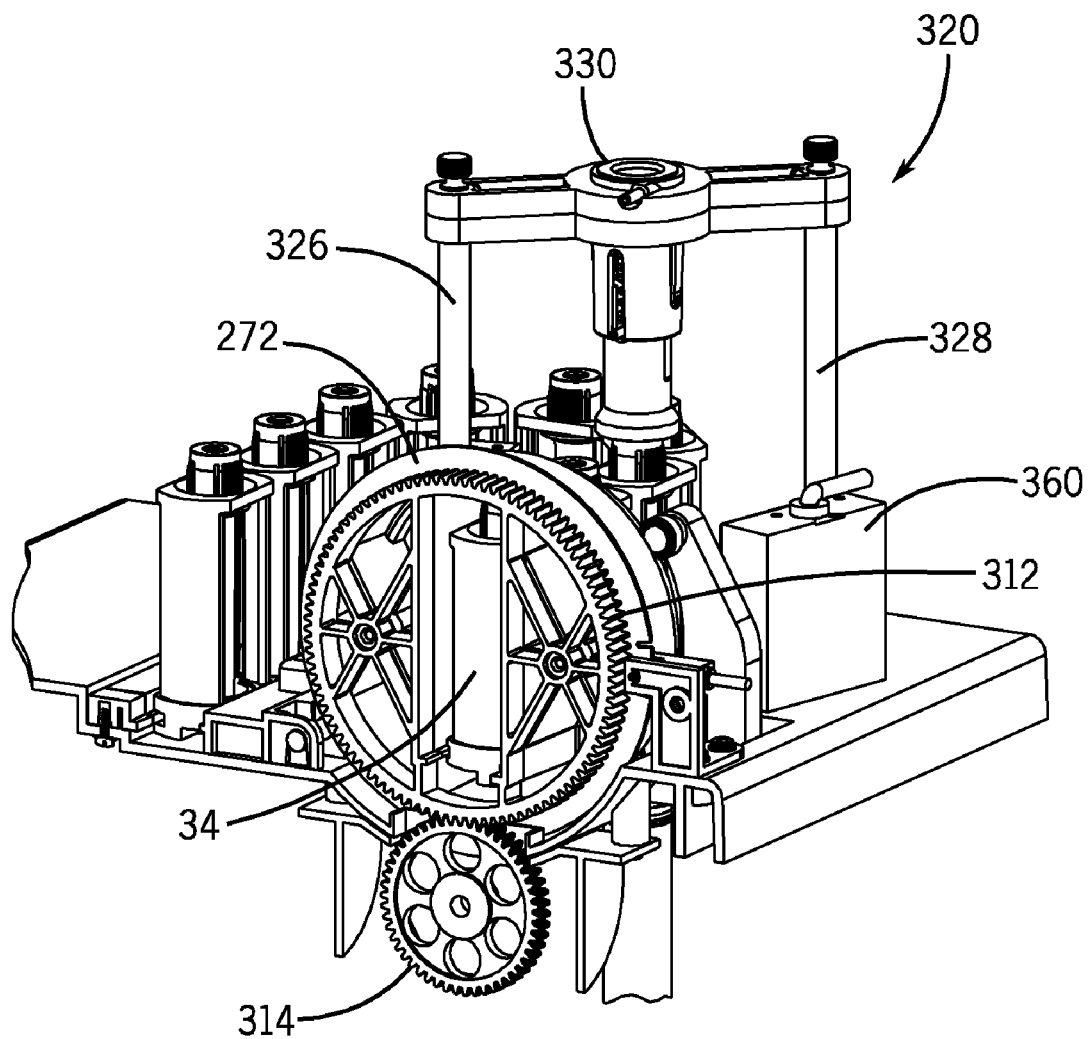
FIG. 26 is a sectional view through the mixing drum of the module for staging sample tubes and mixing the samples in the sample tubes shown in FIGS. 22, 23, 24, and 25.

In order to transport the sample tube carrier 34 along the track 270, the motor (not shown) is actuated, thereby causing the hub 284 and the sample tube carrier drive wheel 282 to rotate. It should be noted that there must be a sufficient number of sample tube carriers 34 on the track 270 so that rotation of the hub 284 and the sample tube carrier drive wheel 282 will move a given sample tube carrier 34 by pushing the other sample tube carriers 34 on the track. It is preferred that all positions of the track 270 where a sample tube carrier 34 can be positioned is occupied by a sample tube carrier 34. The sample tube carrier 34 containing the sample tube "T" is then transported along the track 270 from the sample tube loading position "LP" into the opening 296. The mixing drum 272 shown in FIGS. 23, 24, 25, and 26 can accommodate two sample tube carriers 34, each sample tube carrier 34 containing a sample tube "T". The mixing drum 272 is rotated about its central axis to mix the sample in the sample tube "T". As shown in FIGS. 24, 25, and 26, at any particular time, two sample tubes can be in the mixing drum 272. The sample tube carrier 34 and the sample tube "T" contained in the sample tube carrier 34 are rotated end-over-end during each mixing operation.

After the sample has been mixed for a sufficient amount of time in the mixing drum 272, the sample tube carrier 34 and the sample tube "T" contained therein emerge from the opening 294 in the mixing drum 272 and are transported along the track 270 to the readers 360. The readers 360 read the barcode label on the sample tube "T", after which reading the sample tube carrier 34 and the sample tube "T" contained therein are transported to the sample tube piercing assembly 320. The cap "C" of the sample tube "T" is pierced by means of the piercing element 322. It should be noted that the recessed area of the track 270 at this position must have an opening (not shown) formed therein, so that the piston 348 of the lower portion 336 of the cap-piercing mechanism 332 can pass through this opening and into the opening 52 in the base 44 of the sample tube carrier 34.

Figure 30:
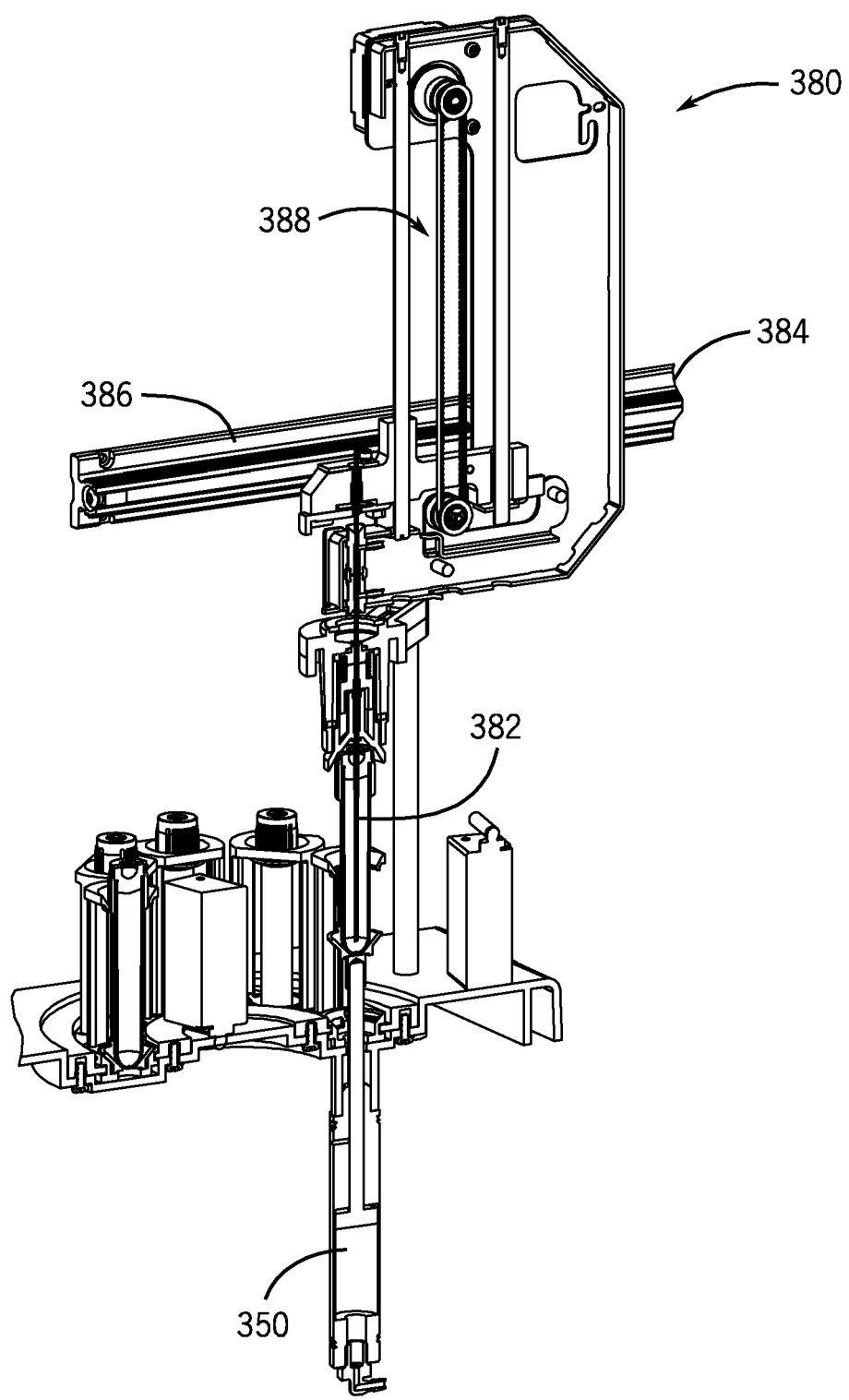
FIG. 30 is a cross-sectional view of the aspiration head shown in FIG. 29 in the open mode position.

The piston 348 is extended vertically in an upward direction and pushes the sample tube bottom retainer 42 a sufficient distance upwardly until the piercing element 322 of the sample tube piercing assembly 320 punctures the cap "C" of the sample tube "T". The piston 348 is then retracted vertically in a downward direction, whereupon the sample tube bottom retainer 42 is lowered vertically in a downward direction until it contacts the base 44. The resilient biasing element 342 pushes the sample tube "T" downwardly so that the sample tube "T" continues to rest on the sample tube bottom retainer 42. The piercing element 322 is typically a needle having a hollow bore. The aspiration probe of the automated clinical analyzer is capable of passing through the hollow bore of the needle to reach the sample in the receptacle "R" of the sample tube "T". After the cap "C" of the sample tube "T" has been pierced, the aspiration probe is actuated to remove a portion of the sample from the sample tube so that a diagnostic assay can be carried out in the automated clinical analyzer. Aspiration probes are discussed in U.S. Pat. No. 5,812,419, incorporated herein by reference. In general, with reference to FIGS. 28, 29, and 30, an aspiration probe assembly 380 comprises an aspiration probe 382, a drive assembly 384 for moving the aspiration probe assembly 380 along a slide assembly 386, and a vertical drive assembly 388 for raising and lowering the aspiration probe 382. The aspiration probe drive assembly 384 moves the aspiration probe 382 over the sample tubes "T" so that the aspiration probe 382 can enter the sample tube "T" to aspirate or deposit liquid. The vertical drive assembly 388 causes the aspiration probe 382 to slide through the hollow bore in the piercing element 322 into the sample tube "T" to aspirate the sample. U.S. Pat. No. 5,812,419 provides additional details relating to the pumps and other mechanisms of the aspiration probe 382. After the sample is aspirated from the sample tube "T", the sample tube "T" in the sample carrier 34 is transported along the track 270 by means of the sample tube carrier drive mechanism. At a desired position (sample tube removal position "RP"), the sample tube "T" can be removed from the sample tube carrier 34 and placed into a sample tube rack 132 or into a sample tube carrier 34 on the track system 32 for delivery to another analysis station or storage. It should be noted that the recessed area of the track 270 at the position "RP" desired for removal of the sample tube "T" from the sample tube carrier 34 position must have an opening (not shown) formed therein, so that the piston 224 of the sample tube lifter 210 can pass through this opening and into the opening 52 in the base 44 of the sample tube carrier 34. The presence of this opening enables the sample tube receiver 172 and the sample tube lifter 210 to carry out the procedure described previously in conjunction with FIGS. 21A, 21B, 21C, 21D, 21E, 21F, 21G, 21H, and 21I.

Removal of the sample tube "T" and placement of the sample tube "T" into a sample tube rack 132 or into a sample tube carrier 34 on the track system 32 by means of the sample tube receiver 172 and the sample tube lifter 210 is carried out in accordance with the procedure described previously in conjunction with FIGS. 21A, 21B, 21C, 21D, 21E, 21F, 21G, 21H, and 21I.

The operations and procedures described herein require the use of a computer, software associated with the computer, signal generators, and other components required for automated functioning of the system. Examples of these types of equipment, including software, are well-known to those having ordinary skill in the art of laboratory automation systems.

In addition, the automated clinical analyzer(s) associated with the apparatus described herein would be expected to provide the source(s) of air, the source(s) of vacuum, the source(s) of electrical power, and the aforementioned computer(s), software, and automation components that would be need to operate the apparatus described herein.

Examples of equipment for the tracks 270, track systems 32, and mechanisms for driving sample tube carriers 34 along the tracks 270 and the track systems 32 are well-known to those having ordinary skill in the art of laboratory automation systems.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A sample tube carrier comprising:
    an elongated body having an upper portion and a lower portion;
    a base coupled to the lower portion; and
    a bottom retainer slidably coupled to the body to slide along at least a portion of a length of the body to move a sample tube contained in the sample tube carrier relative to the body, the sample tube carrier capable of holding a sample tube as the sample tube is transported into a mixing drum, wherein a sample in the sample tube can be mixed by rotating the sample tube carrier and the sample tube held therein in an end-over-end manner in the mixing drum while the sample tube carrier is not attached to any other sample tube carriers.

2. The carrier of claim 1, wherein the carrier has a base having an opening therein to enable a piston positioned externally of the carrier to elevate or lower the sample tube in the sample tube carrier.

3. A sample tube carrier comprising:
    an elongated body having an upper portion and a lower portion;
    a base coupled to the lower portion; and
    a bottom retainer slidably coupled to the body to slide along at least a portion of a length of the body to move a sample tube contained in the sample tube carrier relative to the body.

4. A sample tube carrier as defined in claim 3, wherein the body includes one or more projections and the base includes one or more slots, the projections engageable in the slots to couple the body and the base.

5. A sample tube carrier as defined in claim 3, wherein the body includes one or more grooves and the bottom retainer includes one or more tabs, the tabs slidably receivable in the grooves to couple the body and the bottom retainer.

6. A sample tube carrier as defined in claim 5, wherein the one or more grooves extend along an inner surface of the body and the bottom retainer is displaceable along the inner surface of the body to change a distance between the bottom retainer and the base.

7. A sample tube carrier as defined in claim 3, wherein the upper portion has an opening for receiving a sample tube.

8. A sample tube carrier as defined in claim 7, wherein the opening has a beveled edge.

9. A sample tube carrier as defined in claim 3, wherein the bottom retainer has a concave surface to engage a bottom of a sample tube.

10. A sample tube carrier as defined in claim 3, wherein the bottom retainer is displaceable relative to the base and a change in a distance between the bottom retainer and the base changes a distance above a surface of the body a sample tube contained in the carrier extends.

11. A sample tube carrier as defined in claim 3, wherein the base includes a groove to engage a guide rail of a track along which the sample tube carrier is transportable.

12. A sample tube carrier as defined in claim 3, wherein the base includes an opening to provide access for a piston to move the bottom retainer with respect to the base.

13. A sample tube carrier as defined in claim 3, wherein the bottom retainer is receivable in the base.

14. A method of mixing a sample contained in a sample tube, the method comprising:
    inserting the sample tube into a sample tube carrier, the sample tube carrier having an elongated body having an upper portion and a lower portion and a bottom retainer slidably coupled to the body to slide along at least a portion of a length of the body between the upper portion and the lower portion;
    sliding the bottom retainer toward the lower portion as the sample tube is inserted into the sample tube carrier;
    moving the sample tube carrier along a track;
    inserting the sample tube carrier into a mixing drum; and
    rotating the sample tube carrier and the sample tub in an end-over-end manner to mix the sample.

15. A method as defined in claim 14, wherein the sample tube carrier is inserted into a first opening of the mixing drum and further comprising removing the sample tube carrier from a second opening of the mixing drum.

16. A method as defined in claim 14 further comprising while rotating the sample tube carrier and the sample tube, rotating a second sample tube carrier and a second sample tube in the mixing drum.

17. A method as defined in claim 14 further comprising elevating the bottom retainer toward the upper portion to raise the sample tube.

18. A method as defined in claim 17 further comprising actuating a piston to elevate the bottom retainer.

19. A method as defined in claim 14 further comprising puncturing a cap of the sample tube and aspirating at least a portion of the sample.

20. A method as defined in claim 14 further comprising placing the sample tube onto a module for staging the sample tube by moving the sample tube in at least two directions.

* * * * *